US012773347B2

(12) United States Patent
Hajishah et al.

(10) Patent No.: US 12,773,347 B2
(45) Date of Patent: Oct. 27, 2026

(54) APPARATUS, SYSTEM, AND METHOD OF GAS INFUSION TO ALLOW FOR PRESSURE CONTROL OF IRRIGATION IN A SURGICAL SYSTEM

(71) Applicant: Johnson & Johnson Surgical Vision, Inc., Santa Ana, CA (US)

(72) Inventors: Abraham Hajishah, Irvine, CA (US); Edith Fung, Diamond Bar, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 546 days.

(21) Appl. No.: 17/220,801

(22) Filed: Apr. 1, 2021

(65) Prior Publication Data

US 2022/0313488 A1 Oct. 6, 2022

(51) Int. Cl.

| | |
|---|---|
| ***A61F 9/007*** | (2006.01) |
| ***A61M 1/00*** | (2006.01) |
| ***A61M 39/10*** | (2006.01) |

(52) U.S. Cl.

CPC ......... *A61F 9/00736* (2013.01); *A61M 1/774* (2021.05); *A61M 1/85* (2021.05);

(Continued)

(58) Field of Classification Search

CPC .... A61M 2205/3334; A61M 2205/502; A61M 2210/0612; A61M 1/774; A61M 1/85;

(Continued)

(56) References Cited

U.S. PATENT DOCUMENTS

| | | | |
|---|---|---|---|
| 1,455,235 | A | 5/1923 | Townsend et al. |
| 2,208,550 | A | 7/1940 | Shapiro |

(Continued)

FOREIGN PATENT DOCUMENTS

| | | | |
|---|---|---|---|
| EP | 1356834 | A2 | 10/2003 |
| EP | 1428541 | A2 | 6/2004 |

(Continued)

OTHER PUBLICATIONS

Alcon, Centurion Vision System: Insights and Experiences on Leveraging Innovative Phaco Technology, 2015, 8 pages.

(Continued)

*Primary Examiner* — Kami A Bosworth
*Assistant Examiner* — Avery Smale

(57) ABSTRACT

A surgical system is provided that includes a spike suitable for insertion into a fluid reservoir containing a surgical fluid and a gas pressure pocket. The spike provides the surgical fluid from the fluid reservoir to a surgical pack and provides pressurized gas from a pressure gas source to the fluid reservoir. The surgical system includes a controller that enables operation of the pressure gas source if an output of the pressurized gas is within a pre-determined range. The controller disables the operation of the pressure gas source if the output of the pressurized gas reaches an amount outside of the pre-determined range that causes a critical error. The controller iteratively modifies the surgical system (Continued)

if the output of the pressurized gas is between the pre-determined range and the amount outside of the pre-determined range that causes a critical error until the output is brought within the pre-determined range.

15 Claims, 17 Drawing Sheets

(52) U.S. Cl.
CPC ... *A61M 39/105* (2013.01); *A61M 2205/3334* (2013.01); *A61M 2205/502* (2013.01); *A61M 2210/0612* (2013.01)

(58) Field of Classification Search
CPC .... A61M 39/105; A61M 1/77; A61M 5/1414; A61M 5/1415; A61M 5/1417; A61M 5/155; A61M 5/16822; A61M 2205/3341; A61M 5/162; A61M 1/772; A61M 3/0233; A61M 3/0237; A61M 2005/1402; A61M 2005/14208; A61M 5/168; A61M 5/16854; A61M 5/16881; A61M 2205/3331; A61M 2205/3337; A61M 2205/3344; A61M 2205/70; A61M 2205/15; A61F 9/00736
See application file for complete search history.

(56) References Cited

U.S. PATENT DOCUMENTS 2,373,124 A 4/1945 Frank
2,413,710 A 1/1947 Jason
2,542,461 A 2/1951 Bay
2,716,517 A 8/1955 Tollberg
2,844,351 A 7/1958 Charles et al.
2,954,806 A 10/1960 Kerr
3,693,613 A 9/1972 Kelman
3,812,855 A 5/1974 Banko
3,838,691 A 10/1974 Paludan et al.
3,931,818 A 1/1976 Goldowsky
3,973,602 A 8/1976 Kruse
4,052,987 A 10/1977 Wuchinich et al.
4,156,187 A 5/1979 Brumbach et al.
4,180,074 A 12/1979 Murry et al.
4,186,848 A 2/1980 Walter
4,221,308 A 9/1980 Goodall
4,292,969 A 10/1981 Raible et al.
4,328,803 A 5/1982 Pape
4,343,824 A 8/1982 Caldwell
4,361,148 A 11/1982 Shackleford et al.
4,425,123 A 1/1984 Di Salvo
4,548,205 A 10/1985 Armeniades et al.
4,570,898 A 2/1986 Staeubli
4,620,564 A 11/1986 Ekholmer
4,813,927 A 3/1989 Morris et al.
4,832,685 A 5/1989 Haines
4,841,984 A 6/1989 Armeniades et al.
4,900,301 A 2/1990 Morris et al.
4,921,477 A 5/1990 Davis
4,926,856 A 5/1990 Cambio, Jr. et al.
5,032,111 A 7/1991 Morris et al.
5,047,009 A 9/1991 Morris et al.
5,112,019 A 5/1992 Metzler et al.
5,176,629 A 1/1993 Kullas et al.
5,221,272 A 6/1993 Proni
5,234,038 A 8/1993 Mitchell et al.
5,242,404 A 9/1993 Conley et al.
5,246,422 A 9/1993 Favre
5,341,836 A 8/1994 Doherty
5,342,293 A 8/1994 Zanger
5,360,398 A 11/1994 Grieshaber et al.
5,403,276 A 4/1995 Schechter et al.
5,417,246 A 5/1995 Perkins et al.
5,429,601 A 7/1995 Conley et al.
5,563,584 A 10/1996 Rader et al.
5,593,385 A 1/1997 Harrison et al.
5,593,392 A 1/1997 Starchevich
5,624,394 A 4/1997 Barnitz et al.
5,649,905 A 7/1997 Zanger et al.
5,676,650 A 10/1997 Grieshaber et al.
5,697,898 A 12/1997 Devine
5,700,240 A 12/1997 Barwick, Jr. et al.
5,733,256 A 3/1998 Costin
5,766,146 A 6/1998 Barwick, Jr.
5,795,328 A 8/1998 Barnitz et al.
5,810,765 A 9/1998 Oda
5,830,176 A 11/1998 Mackool
5,865,764 A 2/1999 Moorhead
5,910,110 A 6/1999 Bastable
5,954,971 A 9/1999 Pages et al.
6,013,049 A 1/2000 Rockley et al.
6,024,720 A 2/2000 Chandler et al.
6,083,193 A 7/2000 Kadziauskas et al.
6,149,621 A 11/2000 Makihara
6,159,175 A 12/2000 Strukel et al.
6,179,808 B1 1/2001 Boukhny et al.
6,241,700 B1 6/2001 Leukanech
6,261,283 B1 7/2001 Morgan et al.
6,261,297 B1 7/2001 Kadziauskas et al.
6,280,408 B1 8/2001 Sipin
6,283,937 B1 9/2001 Takamatsu et al.
6,290,690 B1 9/2001 Huculak et al.
6,391,000 B1 5/2002 Belikan et al.
6,491,661 B1 12/2002 Boukhny et al.
6,511,454 B1 1/2003 Nakao et al.
6,527,745 B1 3/2003 Kanda et al.
6,579,255 B2 6/2003 Kadziauskas et al.
6,730,106 B2 5/2004 Kanda et al.
6,780,166 B2 8/2004 Kanda et al.
6,849,059 B2 2/2005 Suzuki et al.
6,875,194 B2 4/2005 Mackool
6,899,694 B2 5/2005 Kadziauskas et al.
6,908,451 B2 6/2005 Brody et al.
6,969,032 B2 11/2005 Olivera et al.
6,997,896 B2 2/2006 Novak
7,001,356 B2 2/2006 Kadziauskas et al.
7,018,355 B2 3/2006 Kadziauskas et al.
7,197,567 B1 3/2007 Fitzgerald
7,544,178 B2 6/2009 Kadziauskas et al.
7,563,242 B2 7/2009 Yaguchi et al.
7,867,191 B2 1/2011 Suzuki
7,967,777 B2 6/2011 Edwards et al.
8,070,712 B2 12/2011 Muri et al.
8,287,486 B2 10/2012 Injev
8,388,582 B2 3/2013 Eubanks et al.
8,679,089 B2 3/2014 Berlin
9,205,186 B2 12/2015 Tarkeshian et al.
9,433,723 B2 9/2016 Steen et al.
9,445,943 B2 9/2016 Wilson et al.
9,511,184 B2 12/2016 Woolford et al.
9,597,445 B2 3/2017 Ha et al.
10,195,316 B2 2/2019 Eddo et al.
10,729,581 B2 8/2020 Boukhny et al.
11,191,668 B2 12/2021 Tarkeshian et al.
2001/0004684 A1 6/2001 Morgan et al.
2002/0019601 A1 2/2002 Wada
2002/0019607 A1 2/2002 Bui
2002/0085952 A1 7/2002 Ellingboe et al.
2003/0163138 A1 8/2003 Nazarifar et al.
2004/0002684 A1 1/2004 Lopez
2004/0108340 A1 6/2004 Witt
2004/0150789 A1 8/2004 Jones
2005/0237503 A1 10/2005 Kubo
2006/0100580 A1 5/2006 Muller
2006/0149301 A1 7/2006 Claus
2008/0114290 A1 5/2008 King et al.
2009/0204080 A1 8/2009 Balteau et al.
2010/0145302 A1 6/2010 Cull et al.
2010/0280434 A1 11/2010 Raney et al.
2010/0280435 A1 11/2010 Raney et al.
2010/0292631 A1 11/2010 Holden et al.
2011/0054385 A1 3/2011 Eichler

(56) References Cited

U.S. PATENT DOCUMENTS

| | | | | |
|---|---|---|---|---|
| 2011/0112472 | A1 | 5/2011 | Jacobson et al. | |
| 2011/0282273 | A1 | 11/2011 | Evans et al. | |
| 2011/0313343 | A1 | 12/2011 | Milutinovic et al. | |
| 2012/0215160 | A1 | 8/2012 | Valenti et al. | |
| 2012/0232466 | A1 | 9/2012 | Kuebler et al. | |
| 2013/0131578 | A1* | 5/2013 | Stalmans | A61F 9/00736 604/66 |
| 2013/0138035 | A1 | 5/2013 | Huculak et al. | |
| 2013/0237900 | A1 | 9/2013 | Hauger | |
| 2013/0245543 | A1 | 9/2013 | Gerg et al. | |
| 2013/0267779 | A1 | 10/2013 | Woolford et al. | |
| 2014/0074013 | A1 | 3/2014 | Mccary et al. | |
| 2014/0114237 | A1 | 4/2014 | Gordon et al. | |
| 2014/0276639 | A1* | 9/2014 | Tarkeshian | A61M 3/0241 604/521 |
| 2016/0095750 | A1 | 4/2016 | Raney et al. | |
| 2016/0100981 | A1* | 4/2016 | Klomp | A61M 39/24 604/290 |
| 2016/0220751 | A1 | 8/2016 | Mallough et al. | |
| 2017/0151090 | A1 | 6/2017 | Raney et al. | |
| 2017/0151092 | A1 | 6/2017 | Raney et al. | |
| 2017/0151376 | A1 | 6/2017 | Raney et al. | |
| 2017/0151377 | A1 | 6/2017 | Raney et al. | |
| 2017/0151378 | A1 | 6/2017 | Raney et al. | |
| 2017/0151379 | A1 | 6/2017 | Raney et al. | |
| 2017/0224888 | A1* | 8/2017 | Hickey | A61M 3/0279 |
| 2017/0273826 | A1 | 9/2017 | Sanchez, Jr. | |
| 2018/0228962 | A1* | 8/2018 | Lin | A61M 3/022 |
| 2019/0321222 | A1 | 10/2019 | Lieu | |
| 2022/0039999 | A1 | 2/2022 | Lieu | |

FOREIGN PATENT DOCUMENTS

| | | | |
|---|---|---|---|
| EP | 3006061 | A1 | 4/2016 |
| WO | 9112034 | A1 | 8/1991 |
| WO | 9418894 | A1 | 9/1994 |
| WO | 0217833 | A1 | 3/2002 |
| WO | 2009112251 | A1 | 9/2009 |
| WO | 2011105909 | A1 | 9/2011 |
| WO | 2012092018 | A1 | 7/2012 |
| WO | 2016122790 | A1 | 8/2016 |
| WO | 2017091643 | A1 | 6/2017 |
| WO | 2018064206 | A1 | 4/2018 |
| WO | 2019068151 | A1 | 4/2019 |
| WO | 2019069201 | A1 | 4/2019 |
| WO | 2019069259 | A1 | 4/2019 |

OTHER PUBLICATIONS

Johansson B, "Adaptive Fluidics: A Complete Game Changer, Automated Aspiration control, Dynamic Infusion Compensation, and a Controlled Surgical Environment," Jun. 2019, pp. 1-2.

Yeu E., "A Clinical Study Review-the Role of Active Fluidics and Torsional Phaco Power in Providing a Stable and Efficient Cataract Surgery Environment," US Ophthalmic Review, Mar. 2018, retrieved from Internet URL: [https://www.touchophthalmology.com/ebooks/ophthalmology/USOPHTH111/index.html?page=34], 12 pages.

* cited by examiner

1100a

1300b

APPARATUS, SYSTEM, AND METHOD OF GAS INFUSION TO ALLOW FOR PRESSURE CONTROL OF IRRIGATION IN A SURGICAL SYSTEM

BACKGROUND

Field of the Disclosure

The present disclosure relates to medical devices and systems, and, more specifically, to an apparatus, system, and method of gas infusion to allow for pressure control of irrigation in a surgical system, such as in a phacoemulsification system.

Description of the Background

Phacoemulsification is a medically recognized technique utilized for crystalline lens removal and is one type of ophthalmic surgery. Phacoemulsification includes making a corneal and/or scleral incision, and the insertion of a phacoemulsification handpiece, which typically includes, at the end thereof, a needle that is ultrasonically driven, in order to emulsify, i.e., to liquefy or break up, the natural crystalline lens and/or an unhealthy aspect, such as a cataract, associated with the patient's eye.

The phacoemulsification handpiece is generally coupled to an irrigation source and an aspiration pump. The handpiece includes the aforementioned distal tip for insertion within the anterior chamber of the patient's eye. This distal end includes the needle, which emits the ultrasonic energy to emulsify the crystalline lens or the unhealthy aspect. The handpiece further includes a sleeve that surrounds at least a portion of the needle. The sleeve comprises at least one irrigation port near the distal end of the sleeve, which is coupled to an irrigation source via an irrigation line, and an aspiration port at the distal tip of the needle, which is coupled to an aspiration pump via an aspiration line. Fluid from the irrigation source, which is typically an elevated bottle or bag of saline solution, is irrigated into the eye via the irrigation line and the irrigation port, and the irrigation fluid and emulsified material are aspirated from the eye by the aspiration pump via the aspiration port and the aspiration line.

Other ophthalmic surgical techniques also typically employ irrigation and aspiration of the eye. Such other ophthalmic procedures may or may not include the destruction, alteration, or removal of features of the natural eye and/or unhealthy aspects of the eye.

As such, ophthalmic surgical systems typically provide a control console to control the aforementioned one or more fluid pressures of the operated surgical instruments. The control console provides the pressure signals for operating the instruments, and may include several different types of human actuatable controllers for controlling these signals. One such actuatable controller is often a footpedal assembly, which the surgeon can use to control the referenced surgical instrumentation.

The irrigation fluid flow controlled during ophthalmic surgeries is the result of the pressure to which the irrigation fluid is subjected. Typically, irrigation pressure is controlled in a sterilized environment through one of three methods—namely gravity, non-contact pumping, or increased head pressure. In order to control irrigation pressure, the industry standard for decades has been the aforementioned use of a gravity-based system in the form of an intravenous pole having thereon a balanced salt solution (BSS) bottle or bag.

In short, the raising of the bottle or bag raises the irrigation pressure on the irrigation fluid based on the enhanced pull of gravity on the contents of the bottle or bag. Of course, this dependence of the fluid source pressure on the height of the intravenous (IV) pole limits the available pressures based on a number of logistical factors, including the height of the ceiling in the surgical room.

As mentioned above, alternate known methodologies may control the pressure by manipulating head pressure at the liquid head within the bottle or bag. Head pressure is typically manipulated by a common technique known as vented gas forced infusion, in which a metal tube is inserted through the bottom of the bottle or bag, is passed through the fluid within the bottle or bag, and the air pocket in the bottle or bag atop the liquid is then pressurized by providing gas through the metal tube to create an increase in head pressure. The head pressure of the fluid may also be depressurized through the drawing of gas through the metal tube.

However, the insertion of a metal tube in order to control head pressure also offers significant disadvantages. For example, the metal tube is expensive to integrate into a consumable pack, and the small orifice and delivery volume does not allow for quick pressurization or depressurization.

Therefore, the need exists to provide an apparatus, system, and method of gas infusion to allow for pressure control of irrigation in a surgical system.

SUMMARY

The embodiments include an apparatus, system and method of controlling the flow rate of an irrigation fluid. The apparatus, system and method include modifying a pressure above the irrigation fluid in a fluid reservoir to increase the flow rate through a surgical pack by iteratively controlling infusion of gas to the fluid reservoir. The iteratively controlling comprises sensing an in-range response to said modifying, wherein the infusion of gas is enabled; and sensing an out-of-range response to said modifying. If, based on prior ones of said modifying: the out-of-range response poses no danger to a patient, the infusion of gas is enabled; the out-of-range response poses a substantial danger to the patient, the infusion of gas is disabled; or the out-of-range response poses no substantial danger to the patient, the iteratively controlling comprises applying a successive series of modifications to correct the out-of-range response. The modifying may comprise a self-testing of a phacoemulsification system; a priming of a phacoemulsification system; or a surgical operation using a phacoemulsification system.

The disclosed apparatus, system and method may also include at least a surgical irrigation system. The disclosed embodiments may include a phacoemulsification console comprising a fluidic controller; an irrigation source comprising surgical fluid; and at least two coextensive ports in fluid communication with the irrigation source, a first of the at least two ports being in fluid communication with the surgical fluid, and a second of the at least two ports being in fluid communication between a gas pressure pocket in the irrigation source and a gas infuser. The gas infuser, under control from the fluidic controller, may infuse gas through the second port to the gas pressure pocket, thereby varying a pressure on the surgical fluid, which in turn varies a flow of the surgical fluid outward from the first port.

More specifically, the embodiments may include an apparatus, system and method of controlling flow pressure applied to an irrigation fluid. The apparatus, system and method may include inserting a multi-port spike into a fluid reservoir containing the irrigation fluid and a gas pressure pocket gravitationally above the surgical fluid, a first port on the spike providing fluid flow of the irrigation fluid from the fluid reservoir opposite the gas pressure pocket to a surgical pack, and a second port on the spike at least partially coextensive with the first port and providing fluidic communication between the gas pressure pocket and a gas infuser; and controlling a flow pressure of the irrigation fluid to the surgical pack by iteratively controlling the output of the gas infuser. The iteratively controlling may include sensing an in-range response to said controlling wherein a surgery proceeds with the gas infuser enabled; or sensing an out-of-range response to said controlling. Upon sensing the out-of-range condition: if, based on prior ones of said controlling, the out-of-range response poses no danger to a patient and allows for a predetermined threshold of responsiveness of the flow pressure to said controlling, the surgery proceeds with the gas infuser enabled; if, based on prior ones of said controlling, the out-of-range response poses a substantial danger to a patient, the gas infuser is disabled; and if, based on prior ones of said controlling, the out-of-range response poses neither no danger nor substantial danger to the patient, the iteratively controlling comprises said controlling applying a successive series of software and, at times as directed by the software, hardware modifications to correct the out-of-range response.

The irrigation source may be an irrigation bottle or bag. The varied pressure may be provided to the gas pressure pocket pursuant to controls by the phacoemulsification console. The controls may be actuated by the user via an interface, such as a graphical user interface or a footpedal.

Thus, the disclosed embodiments provide at least an apparatus, system, and method of gas infusion to allow for pressure control of irrigation in a surgical system.

BRIEF DESCRIPTION OF THE FIGURES

Referring now to the figures incorporated herein, shown are non-limiting embodiments of the present disclosure, wherein like numerals represent like elements, and wherein.

DETAILED DESCRIPTION

Figure 1:
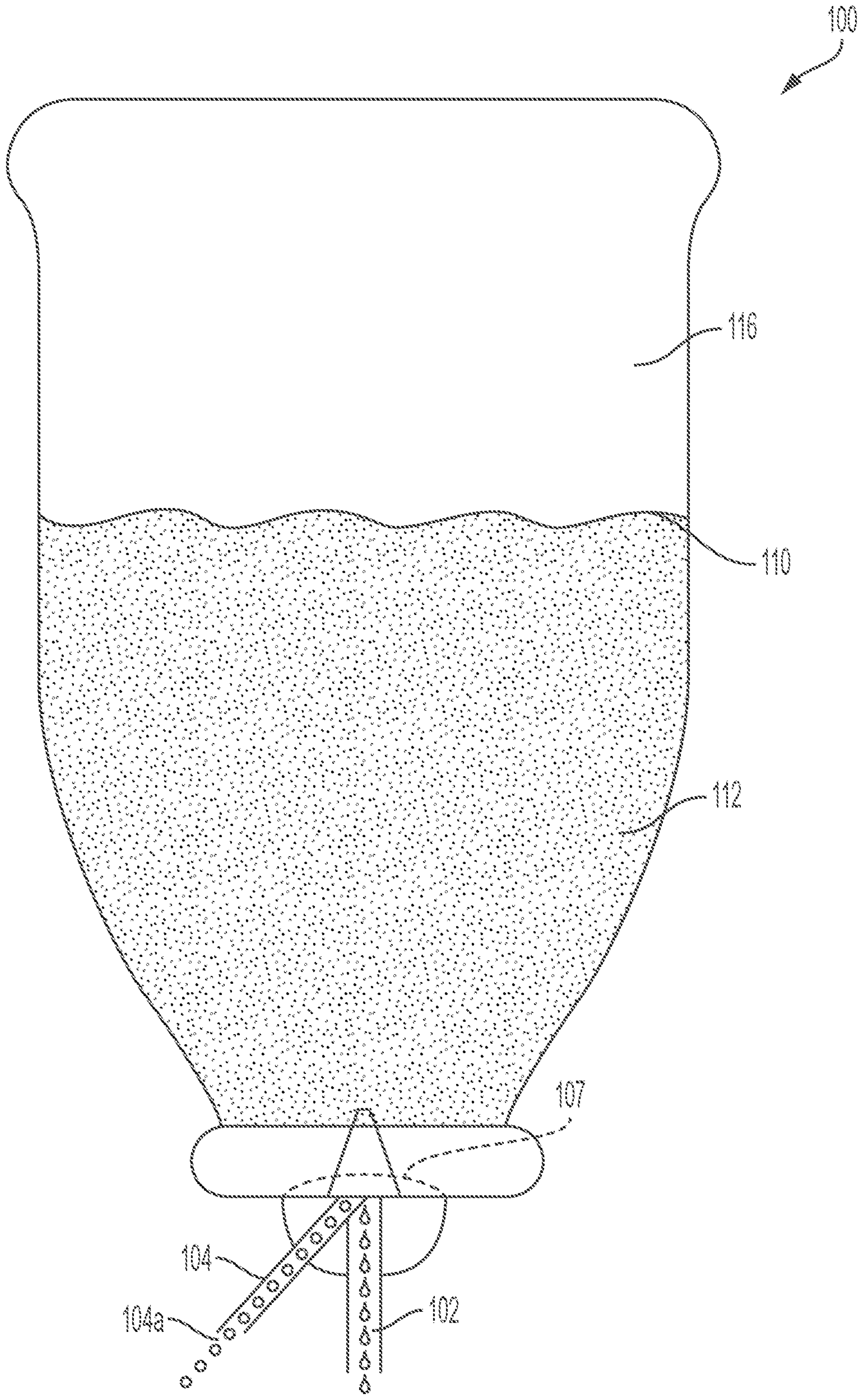
FIG. 1 is a diagram illustrating an exemplary irrigation bag or bottle according to certain of the embodiments.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

The terminology used herein is for the purpose of describing particular exemplary embodiments only and is not intended to be limiting. For example, as used herein, the singular forms “a”, “an” and “the” may be intended to include the plural forms as well, unless the context clearly indicates otherwise. The terms “comprises,” “comprising,” “including,” and “having,” are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being “on”, “engaged to”, “connected to” or “coupled to” another element or layer, it may be directly on, engaged, connected or coupled to the other element or layer, or intervening elements or layers may be present, unless clearly indicated otherwise. In contrast, when an element is referred to as being “directly on,” “directly engaged to”, “directly connected to” or “directly coupled to” another element or layer, there may be no intervening elements or layers present. Other words used to describe the relationship between elements should be interpreted in a like fashion (e.g., “between” versus “directly between,” “adjacent” versus “directly adjacent,” etc.). Further, as used herein the term “and/or” includes any and all combinations of one or more of the associated listed items.

Yet further, although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Thus, terms such as "first," "second," and other numerical terms when used herein do not imply a sequence or order unless clearly indicated by the context. That is, a first element, component, region, layer or section discussed below could be termed a second element, component, region, layer or section without departing from the teachings of the exemplary embodiments.

Certain types of ocular dysfunction, such as cataracts, are commonly treated with surgical procedures, such as to remove the natural lens from the eye and replace it with a clear artificial lens. More particularly and by way of example, phacoemulsification refers to a surgery, often employed when a patient suffers from cataracts, in which the eye's natural lens is emulsified by applying ultrasonic energy to the lens with a handpiece. Once the lens is emulsified, it is aspirated from the eye by applying a vacuum to the handpiece to remove the emulsified lens material via a needle at the distal end of the handpiece. During the procedure, irrigation of the surgical area is performed, and aspirated material/fluid replaced, using a balanced salt solution, thereby maintaining necessary pressure in the interior of the eye. The emulsified, irrigated and aspirated lens is then typically replaced with a clear artificial intraocular lens (IOL).

To perform the afore-discussed and similar procedures, a surgeon often utilizes a computer-controlled system of specialized equipment called a phacoemulsification console to control and execute the ultrasonic emulsification, irrigation, and aspiration of the natural lens of the eye prior to inserting the IOL. Phacoemulsification consoles use various computer programs for performing these various tasks, which are controlled in part by adjusting the settings of these programs to drive piezoelectric crystals, motors, and/or pumps, for example, which are used to emulsify, irrigate, and aspirate the subject lens material and which do other tasks necessary to complete the surgery. These control programs may receive control signals from the system console, and/or from peripheral elements linked to the system console. Such peripheral control elements may include, by way of example, the one or more footpedals referenced above.

During the procedure, information such as the amount of vacuum applied to aspirate, the flow rate, a microscopic view of the operating field, the irrigation pressure, and the like, may be displayed on and at least partially controllable from a graphical user interface (GUI) of the phacoemulsification system console, or on a separate screen, computer, or other viewing device. At least some of this data and functionality may provide feedback to inform and improve current and subsequent procedures.

The embodiments provide at least a gas infused, ported irrigation system for ocular surgery. A balanced salt solution (BSS) reservoir, which may be a bottle or a bag, for example, may readily receive a gas infusion, responsive to one or more control signals, to pressurize and depressurize the fluid pressure at the output of the reservoir. The improved and refined control of the irrigation fluid pressure thus provided allows for a refined control of irrigation in the ocular surgical system, such as in a phacoemulsification system.

More particularly and as illustrated in FIG. 1, a reservoir 100, such as a BSS source reservoir 100, may be provided with two ports 102, 104. One of the ports 102 may be for irrigation, and the other 104 for air or other gas input or withdrawal, such as to create increased pressure at output 102. A fluidic connection between the reservoir 100 and these ports 102, 104 may occur when the ports 102, 104 are inserted to the reservoir 100, such as via a piercing of a cover/stopper 107 that seals the reservoir 100.

The port 104 may allow for the providing of pressure, or depressurization, at least partially coextensive with the output port 102 of the reservoir 100, and/or at the head 110 of the irrigation fluid 112. By way of example, this enhanced pressure or depressurization via gas infusion 104*a* may be provided directly at the output port 102, such as in conjunction with the gravity force on the fluid 112 present at output port 102. In embodiments described herein, gas infusion 104*a* may also be referred to a gas forced infusion or GFI.

The use of the port 104 in the disclosed embodiments may allow for the avoidance of the use of an inserted metal tube to provide increased head pressure, as is done in the known art. The skilled artisan will appreciate that the placement of the port 104 in FIG. 1 is exemplary in nature only, and that port 104 may reside at any point along the reservoir 100, including to provide gas infusion pressurization into the air pocket above the irrigation fluid 112, and/or via one or more tubes that may pass through portions of air pocket and/or through fluid 112.

Accordingly, and unlike other known methodologies of advancing head pressure in a surgical fluid system such as the aforementioned insertion of a metal tube to advance head pressure, the disclosed embodiments enable quick volume pressurization and/or depressurization to output the irrigation (or other surgical) fluid. More particularly, the availability of higher gas flow rates into/out of the reservoir in the disclosed embodiments allows for expedited and improved control, such as by providing both fine and coarse adjustment, of fluid pressure in a surgical system, such as irrigation pressure in a phacoemulsification system.

Figure 2:
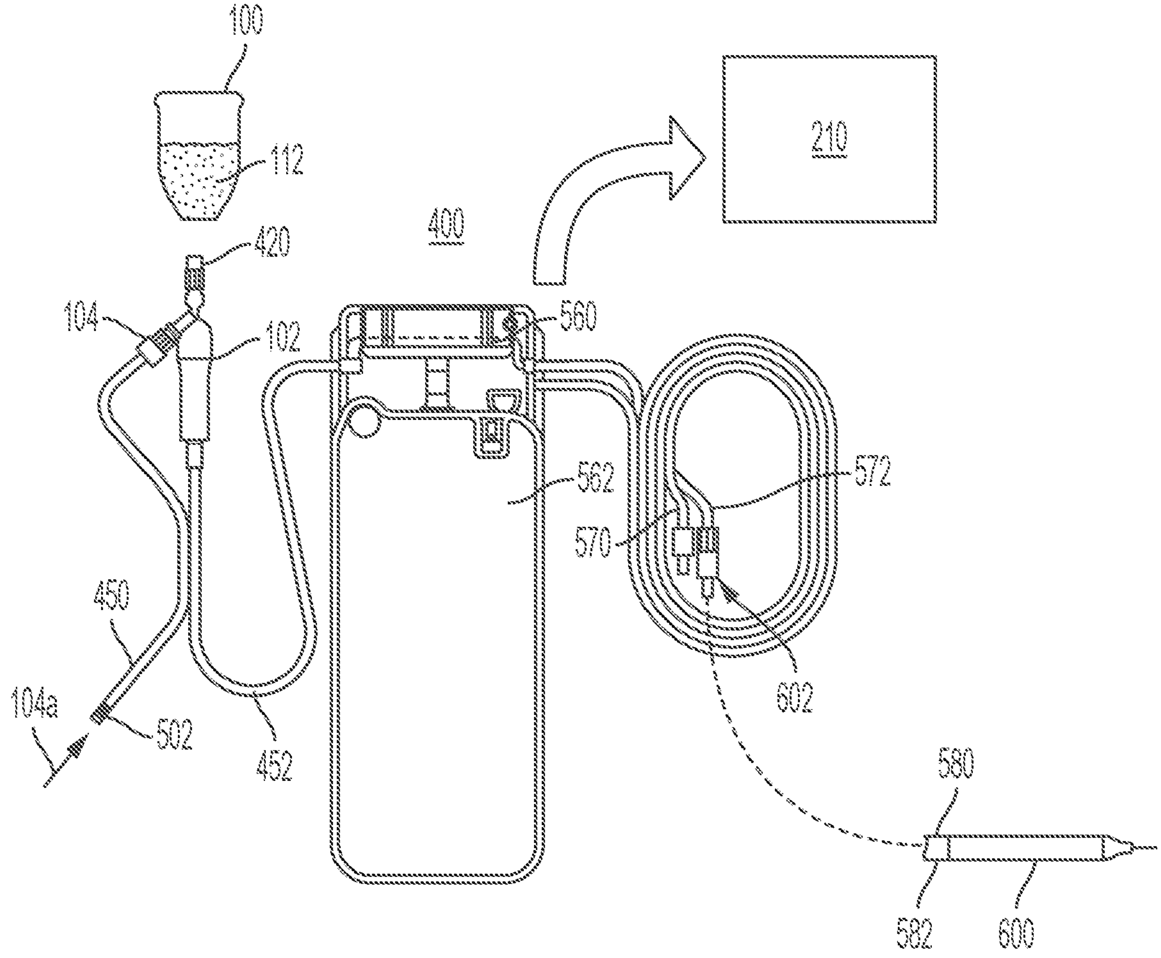
FIG. 2 is an illustration of a surgical pack according to the embodiments.

FIG. 2 illustrates a surgical "pack" or cassette 400 which provides a self-contained system suitable for insertion into a phacoemulsification system 210. The illustrated pack provides a gas infusion 104*a* for pressurization/depressurization at least to the output 102 of, for example, BSS 112 from a BSS bottle reservoir 100 in a surgical system.

Figure 3:
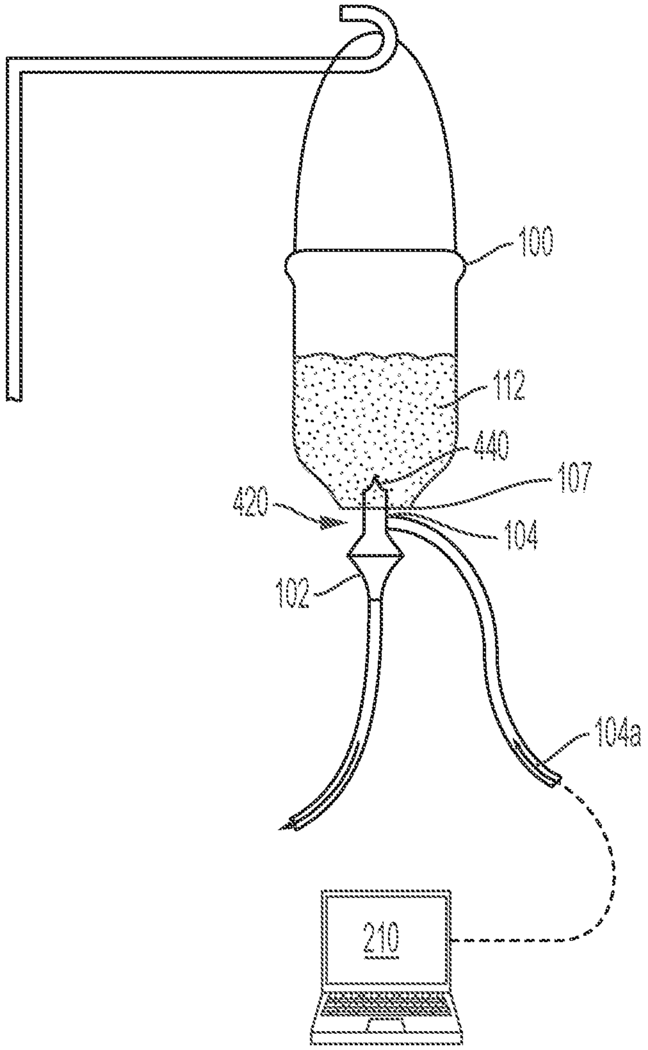
FIG. 3 is an illustration of an insertion of a surgical pack into a surgical console.

FIG. 3 illustrates the connection of spike 420 of pack 400 of FIG. 2 following insertion into, and interconnection with, the BSS reservoir 100. The illustrated console 210 may be, for example, a phacoemulsification console, although the skilled artisan will appreciate that the console 210 may be or include other types of surgical capabilities.

As illustrated in FIGS. 2 and 3, the pack 400 may provide a connection spike 420 for connection to the BSS reservoir 100, and the connection spike 420 may include both a port 102 for the output of BSS fluid 112 from the reservoir 100, and a port 104 for the infusion of gas into the BSS fluid 112 of reservoir 100. Ports 102, 104 may or may not be substantially coextensive.

The BSS reservoir 100 may be a bottle or a bag, as discussed throughout. The infused gas 104*a* may pass through the BSS fluid 112 to the head of the BSS fluid 112 in the BSS reservoir 100 to provide a pressurization and hence increased fluid flow from the bottle to the eye of a patient. Other embodiments are also envisioned, such as where the amount of infused gas 104*a* may be decreased to provide less vacuum resulting in depressurization and a decreased flow rate at the fluid output 102. In another embodiment, the infused gas 104*a* provided via port 104 is directly applied "above" the fluid head to provide a pressurization, may be apparent to those skilled in the pertinent art in light of the disclosure herein.

Figure 4:
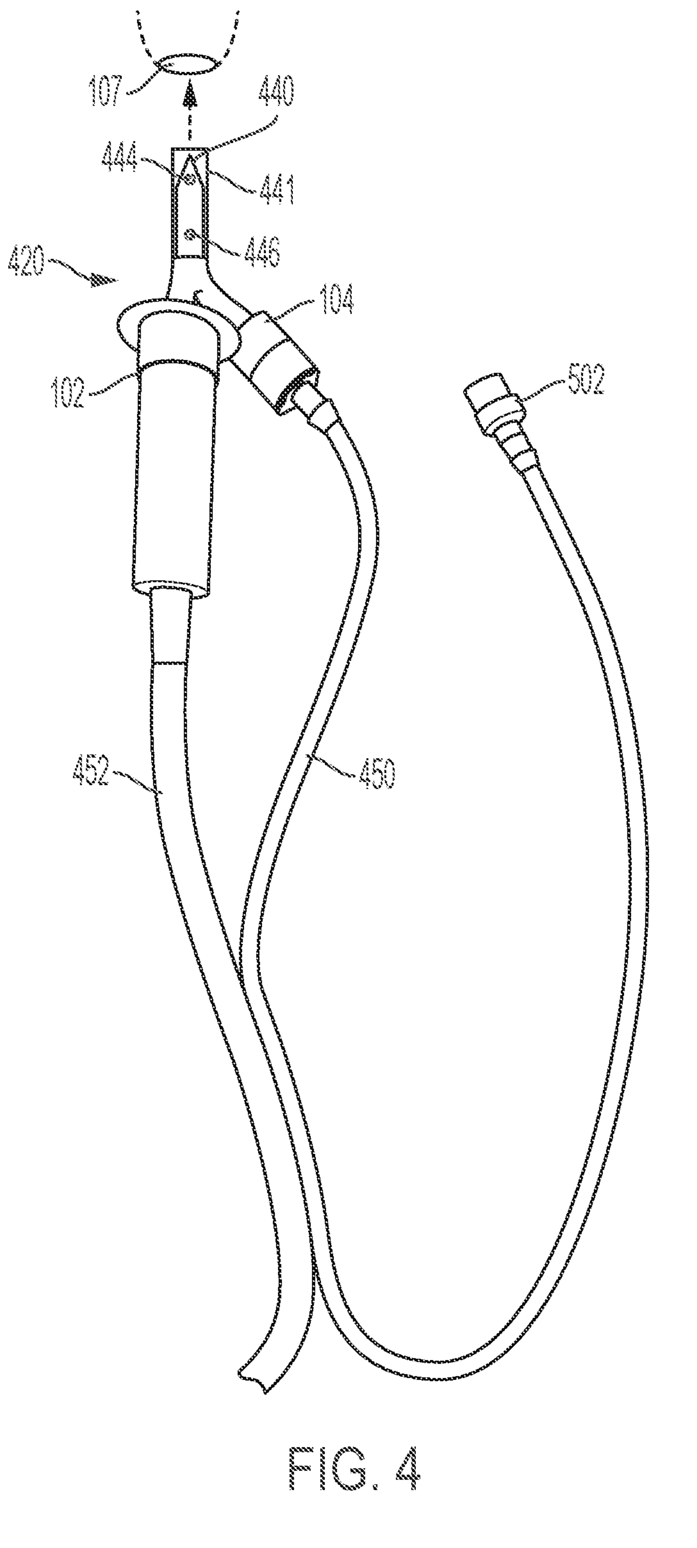
FIG. 4 is an illustration of a surgical connector.

FIG. 4 illustrates, with particularity, an exemplary spike 420 for insertion into a BSS reservoir 100 according to the embodiments. As shown, the spike 420 may include a literal spike 440, such as may be used to pierce a cover or stopper 107 that seals and protects the contents of the BSS reservoir 100. This literal spike 440 may be protectively covered with a safety cover 441 prior to insertion, as shown. Yet further, the literal spike 440 may be of sufficient length so as to extend through the cover and into BSS fluid 112 or through the cover and the BSS fluid 112 into an air pocket above the BSS fluid 112, and may thus have a gas outlet 444 at the point of the literal spike 440 while also have a fluid inlet 446 to the fluid output port 102 at a lower portion of the spike 440 to receive BSS fluid 112 to fluid output port 102. In an embodiment, the location of the fluid inlet 446 and gas outlet 444 may be located anywhere along the literal spike 440. In addition, literal spike 440 may have more than one inlet 446 and gas outlet 444.

Figure 5:
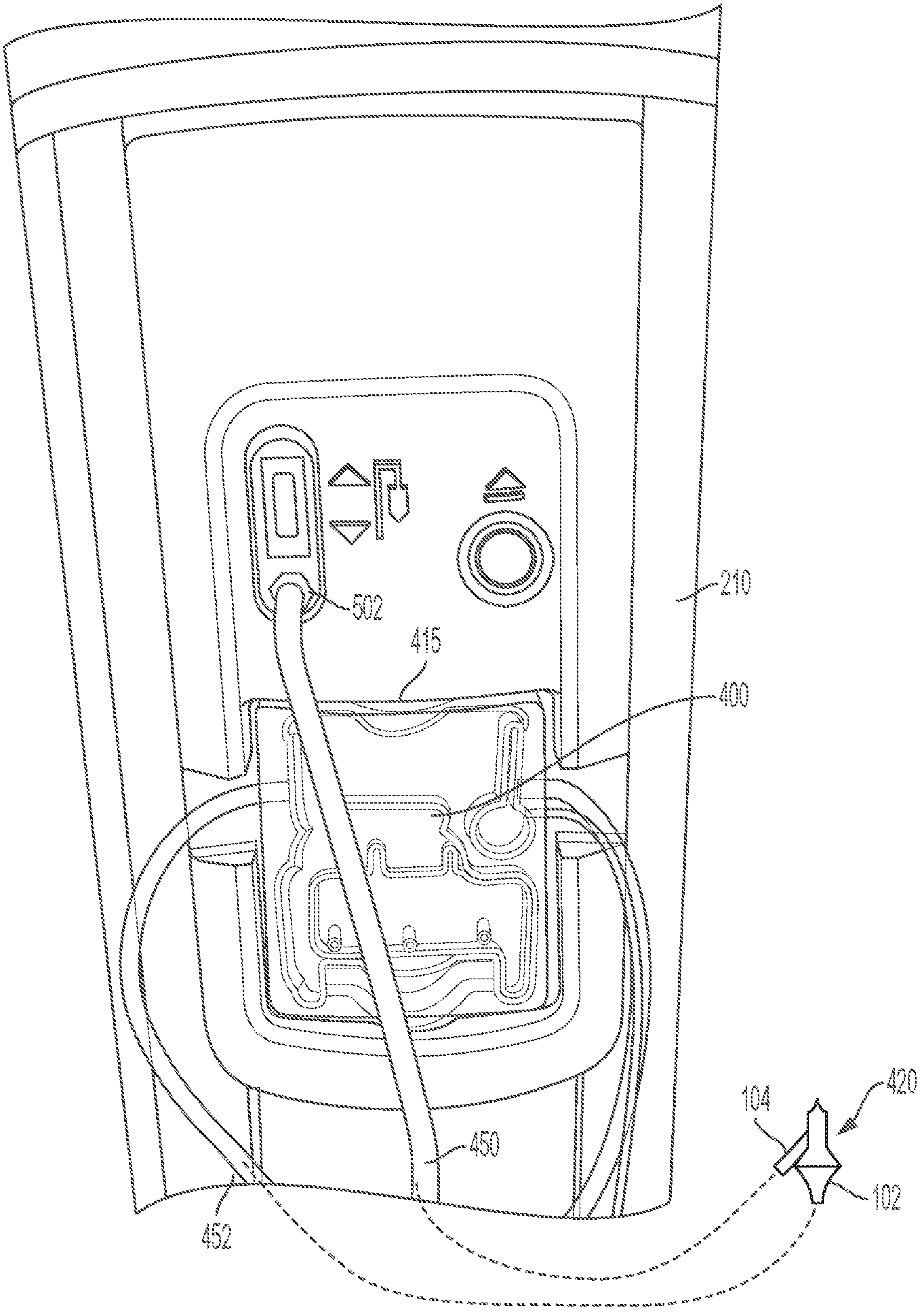
FIG. 5 is an illustration of the insertion of a surgical connector into an irrigation fluid source.

Particularly shown are the gas infusion port 104 and fluid output port 102 of the spike 420, along with tubing lines 450, 452 associated therewith. Although the gas infusion port 104 and the fluid output port 102 are shown as being substantially coextensive in FIG. 4, it will be understood that the ports may be separated, such as wherein the gas infusion port 104 is suitable to run to an upper insertion point to the BSS reservoir 100, and the fluid output port 102 to a lower insertion point on the BSS reservoir 100. FIG. 5 shows with specificity the insertion of a pack 400 having gas infusion port 104 and fluid output port 102 coupled with the console 210.

With reference now to all of the foregoing figures, the gas infusion port 104 may be fluidically communicative, such as via the illustrated infusion line tubing 450, with an infusion gas console connector 504 that connects to, for example, the phacoemulsification console 210 distally from the gas infusion port 104 along the infusion line tubing 450. Of course, the gas input port 104 and the gas console connector 502 may be readily detachable and may be proprietary or non-proprietary in design. The infused gas 104*a*, whether providing pressure or depressurization, may provide the equivalent of a substantial increase in the height of the BSS reservoir 100. The infused gas 104*a* may be air, although other types of gas may additionally be used.

At least partially coextensive with the gas input port 104 on the spike 420 may be the fluid output port 102. BSS fluid 112 may exit the BSS reservoir 100 at the fluid output port 102 and pass through, for example, a fluid tubing line 452 to the pack 400. The pack 400 may include, for example, a pathway 560 for receipt of the BSS fluid 112 from the reservoir 100 and eventual output of the BSS fluid 112 through handpiece 600, and may additionally include, for example, fluid storage bag 562 for receiving aspirated fluid from an eye.

The pack 400 also includes irrigation tubing line 572 and aspiration tubing line 570, which fluidically communicate from the pack 400 to the respective aspiration port 580 and irrigation port 582 of the handpiece 600. Accordingly, the irrigation and aspiration tubing lines 572, 570 terminate in connections to the aforementioned handpiece 600, such as terminating in a luer lock fitting 602 for the irrigation tubing line 572.

Figure 6:
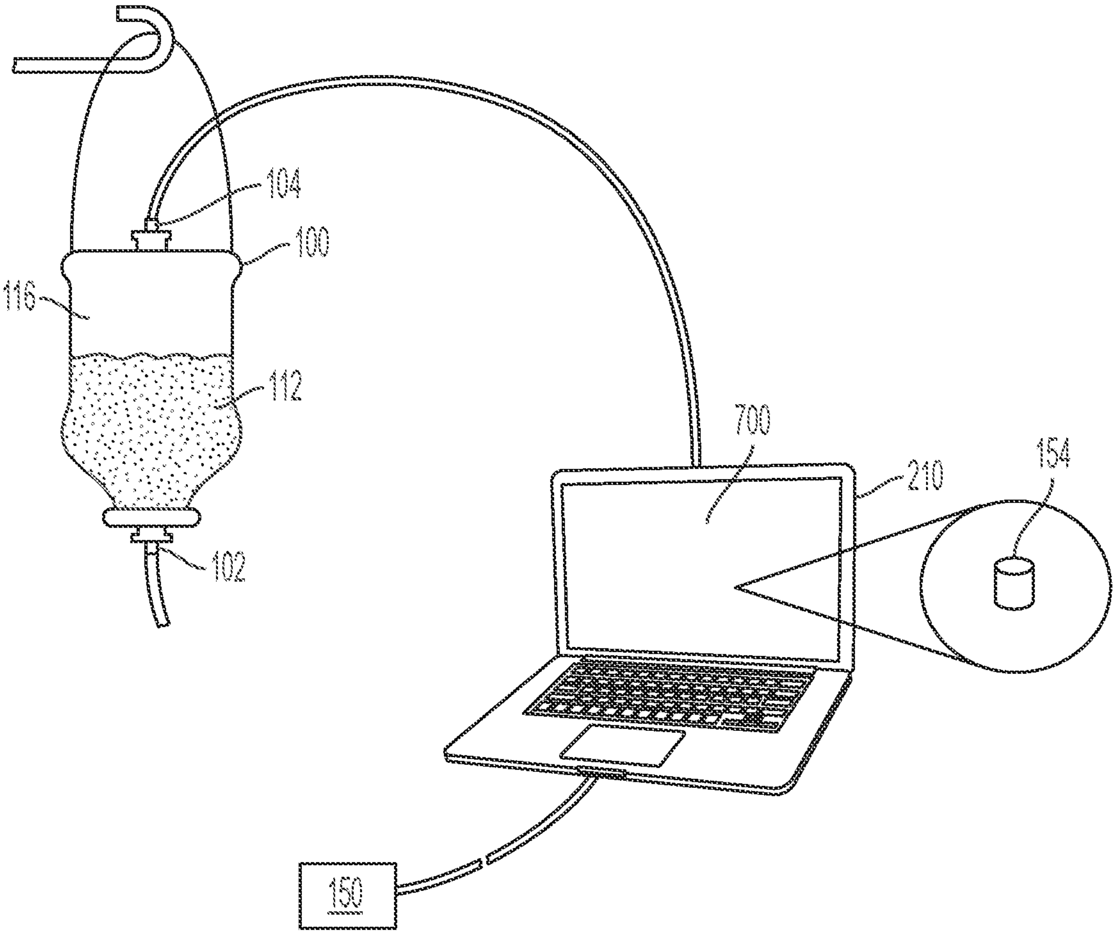
FIG. 6 is an illustration of a surgical system.

FIG. 6 illustrates a dual port 102, 104 irrigation system for control by a surgical console 210, such as a phacoemulsification console. As illustrated, an BSS reservoir 100, such as a balanced salt solution bag or bottle, is provided as a reservoir/fluid source. The BSS reservoir 100 is illustrated as having two ports 102, 104, one for gas infusion and one for fluidic output from the BSS reservoir 100.

In the illustration, the gas infusion port 104 may be provide pressurization to the air pocket 116 of the BSS reservoir 100, such as through the BSS liquid 112 in the reservoir. Thereby, the illustrated upper gas input port 104 allows gas to flow from the pressurization system of phacoemulsification console 210 into the air pocket 116 of the BSS reservoir 100. This air flow accordingly increases or decreased the air pressure placed on the BSS liquid 112 in a ratio correspondent to the volume of air pushed into the BSS reservoir 100 (or withdrawn from the reservoir) by the console 210.

The phacoemulsification console 210 connective to the BSS reservoir 100 may be instructed, either by an operator, such as by actuation of a button, handle, or footpedal 150, or automatically, such as upon reaching a trigger 154 preprogrammed into console 210, to pump gas into, vent gas from, or flow-depressurize, air pocket 116 via the gas output port 104. This actuation of the output port 104 may thus allow the user and/or the console 210 to increase or decrease the pressure on the BSS liquid 112 very quickly, and with both fine and coarse control. This enables an expedited response to any surgical conditions, such as abnormal surgical conditions, i.e., post-occlusion surge, due at least to the improved efficiency in the output port 104 over the known art.

This expedited and refined responsiveness in the head pressure of the BSS liquid allows for a closed-loop dynamic irrigation system, as illustrated in FIG. 6. That is, the response of head pressure to surgical conditions may be automated based on surgical factors monitored by the console 210. As used herein throughout, console may include, by way of example: a user display, as illustrated FIGS. 3 and 6, such as may be capable of providing aspects of the graphical user interface discussed in relation to FIGS. 7-9; at least one processor having associated therewith, for execution by the processor, the algorithms discussed throughout, including those discussed in relation to FIGS. 10-13; and gas inputs and associated ports for gas infusion, aspiration, and irrigation, to provide the functionality discussed throughout.

The surgical factors monitored by console 210 may be based on indications from one or more sensors at, near, or otherwise viewing or measuring parameters of the eye; or may be manual with real-time indications to the operator of surgical conditions. Needless to say, surgical outcomes are consequently improved through the use of the embodiments.

Figure 7:
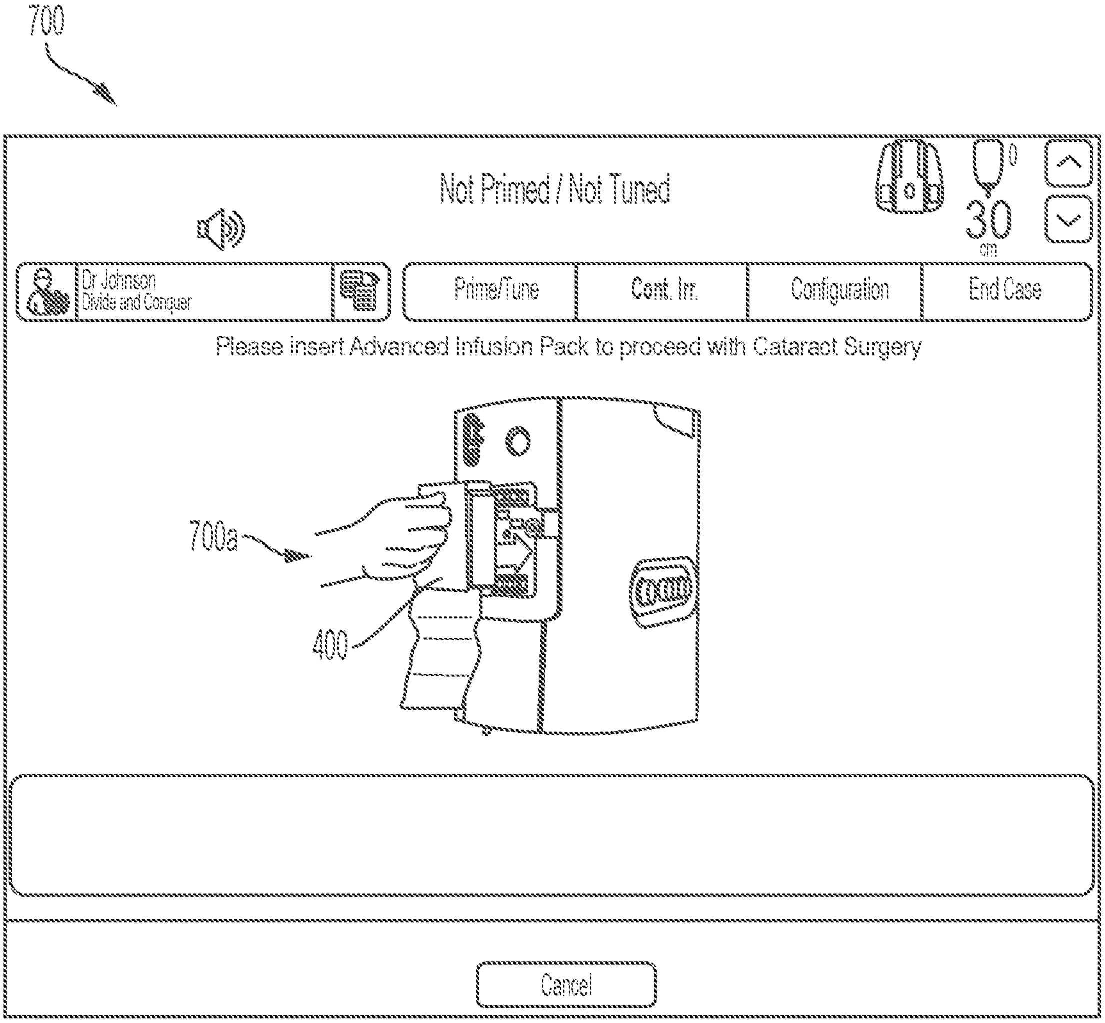
FIG. 7 is an illustration of a graphical user interface.
Figure 8:
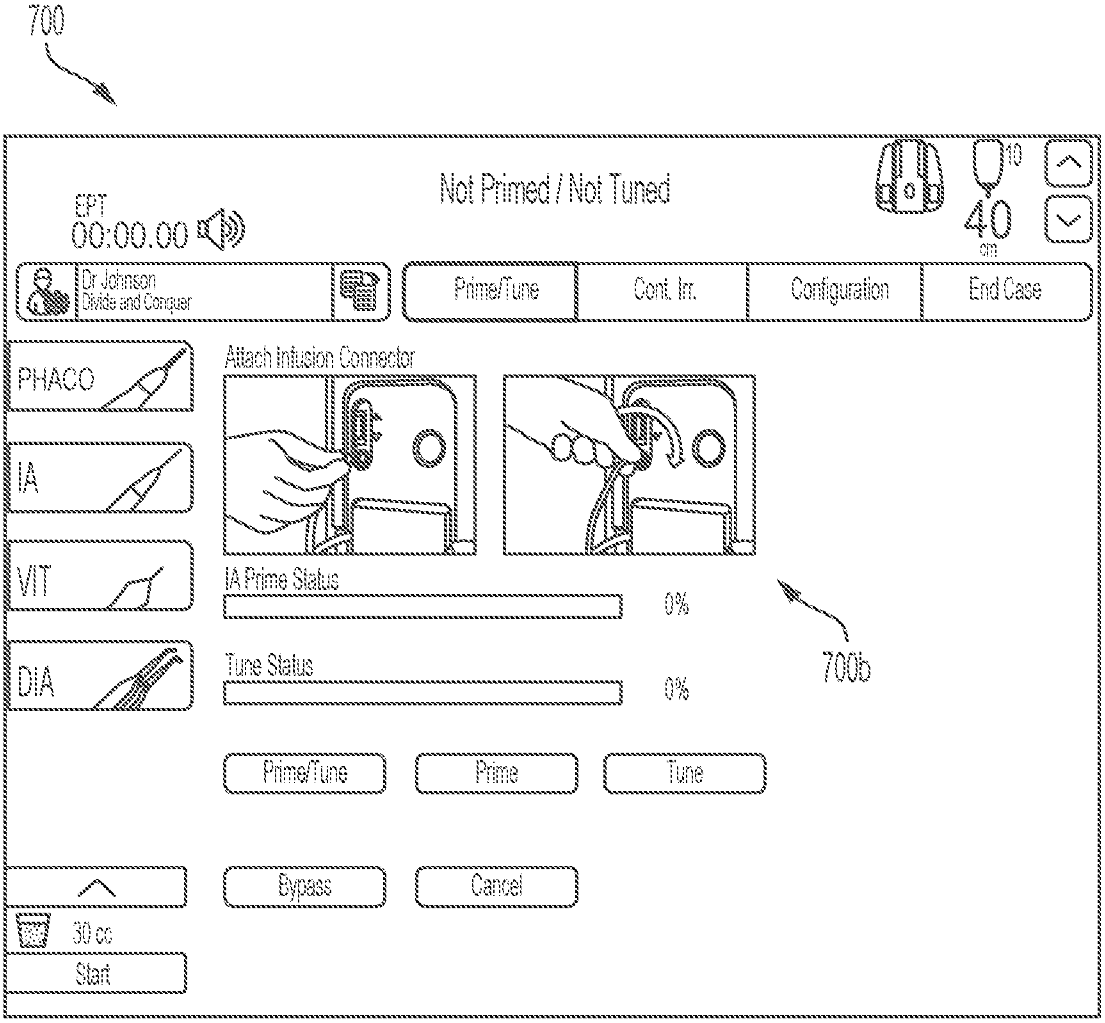
FIG. 8 is an illustration of a graphical user interface.
Figure 9:
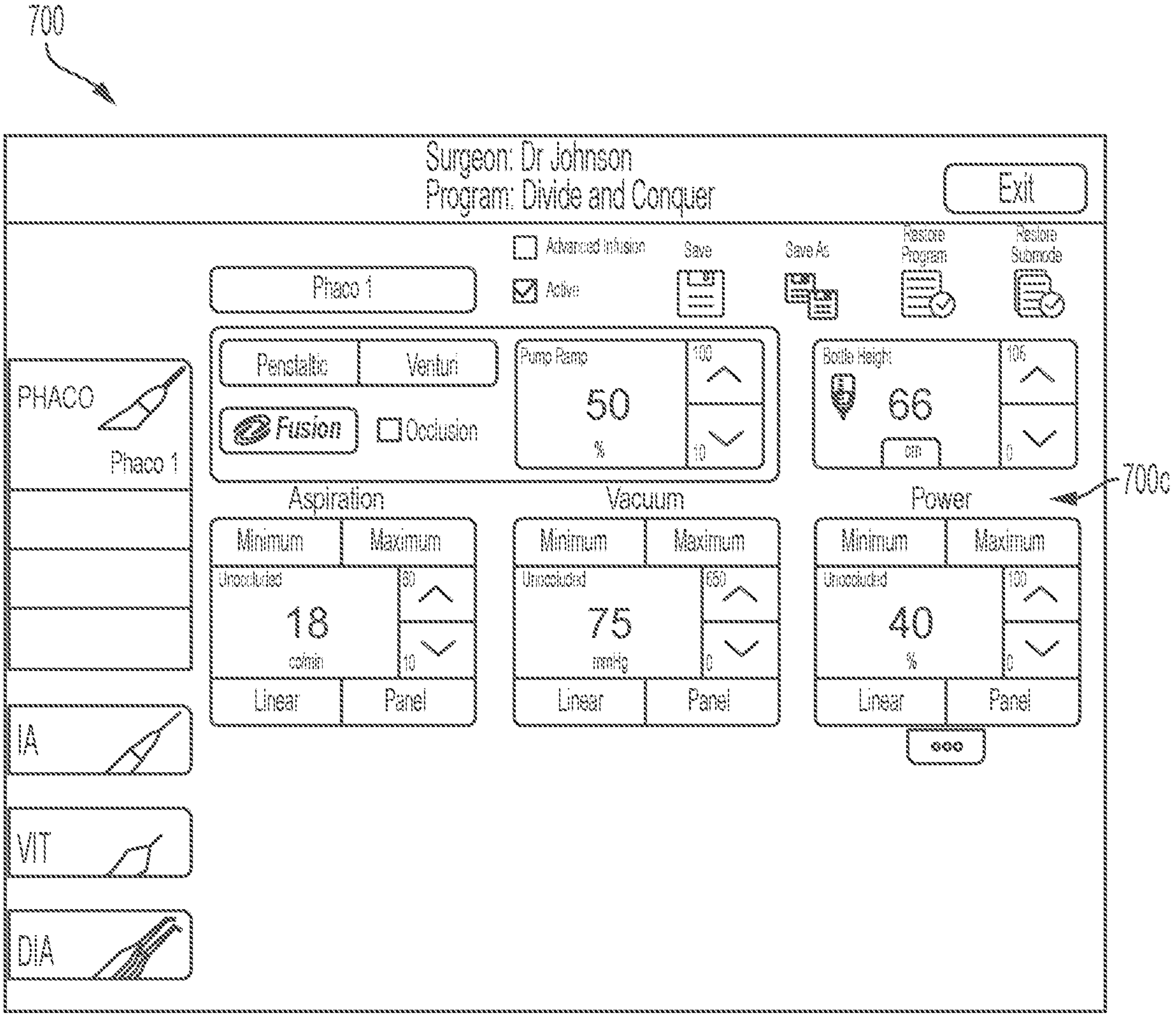
FIG. 9 is an illustration of a graphical user interface.

FIG. 7 illustrates a graphical user interface (GUI) 700 that shows an embodiment 700*a* instructing a user regarding the insertion of pack 400 discussed herein throughout. FIG. 8 shows a different image 700*b* on GUI 700, which instructs an operator as to how to connect and prime the fluid and gas infusion aspects of such a pack 400, as detailed below. The different image 700*c* on GUI 700 shown in FIG. 9 illustrates the myriad of information provided to the operator in the embodiments, such as may allow for manual or automated process modification as discussed throughout.

More specifically, after a surgeon is selected, surgery program options may be presented to a surgeon/user for selection. The GUI 700 may present a variety of options for operating a phacoemulsification system, such as programs, including a surgeon's most-frequently preferred, and/or default, program or programs may be listed.

The pack 400 may then be installed, such as by insertion into the fluidics panel 415 (shown in FIG. 5) until the system activates a latch mechanism to retain the pack. Thereafter, the spike, having ports associated therewith may be connected to the BSS reservoir 100, the gas infusion line 450 may be connected to the console 210 via a gas connector 502 located on an end of the gas infusion line 450, and the irrigation line 572 and aspiration lines 570 may be connected to a handpiece 600 (shown in FIG. 2). The system may then be subjected to priming, as discussed herein followed by the surgical procedure.

Figure 10:
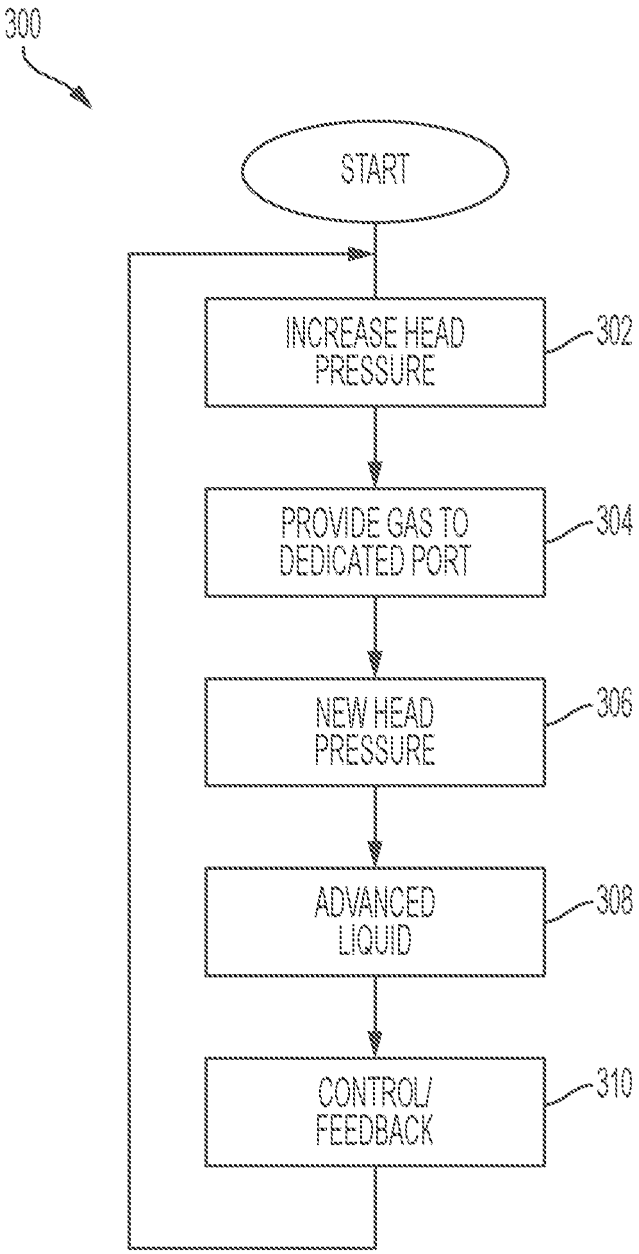
FIG. 10 is a flow diagram illustrating aspects of the embodiments.

FIG. 10 is a flow diagram illustrating a method 300 in accordance with the embodiments. In the illustration, during a surgical procedure at step 302 an instruction to increase pressure in a surgical fluid system is received. The surgical system may be, for example, an irrigation system on a phacoemulsification console.

At step 304, air or another gas is provided by the receiver of the instruction at step 302 to a BSS reservoir via a dedicated port. At step 306, the flow pressure on the fluid in the BSS reservoir is increased commensurate with the air delivered at step 304.

The fluid is advanced, commensurate with the increased pressure delivered at step 306, from a second port not in direct fluid communication with the port at step 308. At step 310, the output of the fluid according to step 308 may be controlled via control signaling, sensing and/or feedback using any known methodologies, such as in-line buffers, port limiters, or the like.

Simply put, the embodiments may thus include control of pressure infusion via a plurality of algorithms using sensing, output readings and/or manual inputs. These algorithms may insure safe, efficient and improved operation of, for example, a phacoemulsification system. This improved operation may include, by way of non-limiting example, application of smoothing algorithms to check pressure and maintain smoothing of the impulses of fluid from the irrigation system.

The above steps are typically presented by the GUI discussed throughout, wherein the GUI and the algorithms are applied by one or more computing processors, such as may execute and include instrument host (IH) 210*a* of console 210, executing a plurality of software code. These algorithms may include code for initial testing and priming of the gas infusion feature, as well as for the control of surgical processes in accordance with in-surgery data.

The software component may thus be applied by a processor-based instrument host 210*a* (shown in FIG. 14), which includes the processor, within surgical console 210. Instructions may be generated to control the software, firmware, and hardware of the fluidics via fluidics controller 210*b* and the gas infusion port 104. Likewise, the GUI provides an interface for user inputs and status displays of the features, including the gas infusion, discussed herein.

As mentioned, the plurality of algorithms using sensing, output readings and/or manual inputs are software-based and are applied by the instrument host 210*a* to the gas infusion 104*a* so as to modify the irrigation pressure. The objective of these algorithms is to enable the providing and maintaining of an equilibrium state between the irrigation and the aspiration of the phacoemulsification system during a surgical procedure. However, the vacuum or aspiration may exceed the irrigation pressure, a situation that may be resolved by creating higher pressure to improve irrigation flow.

Figure 11A:
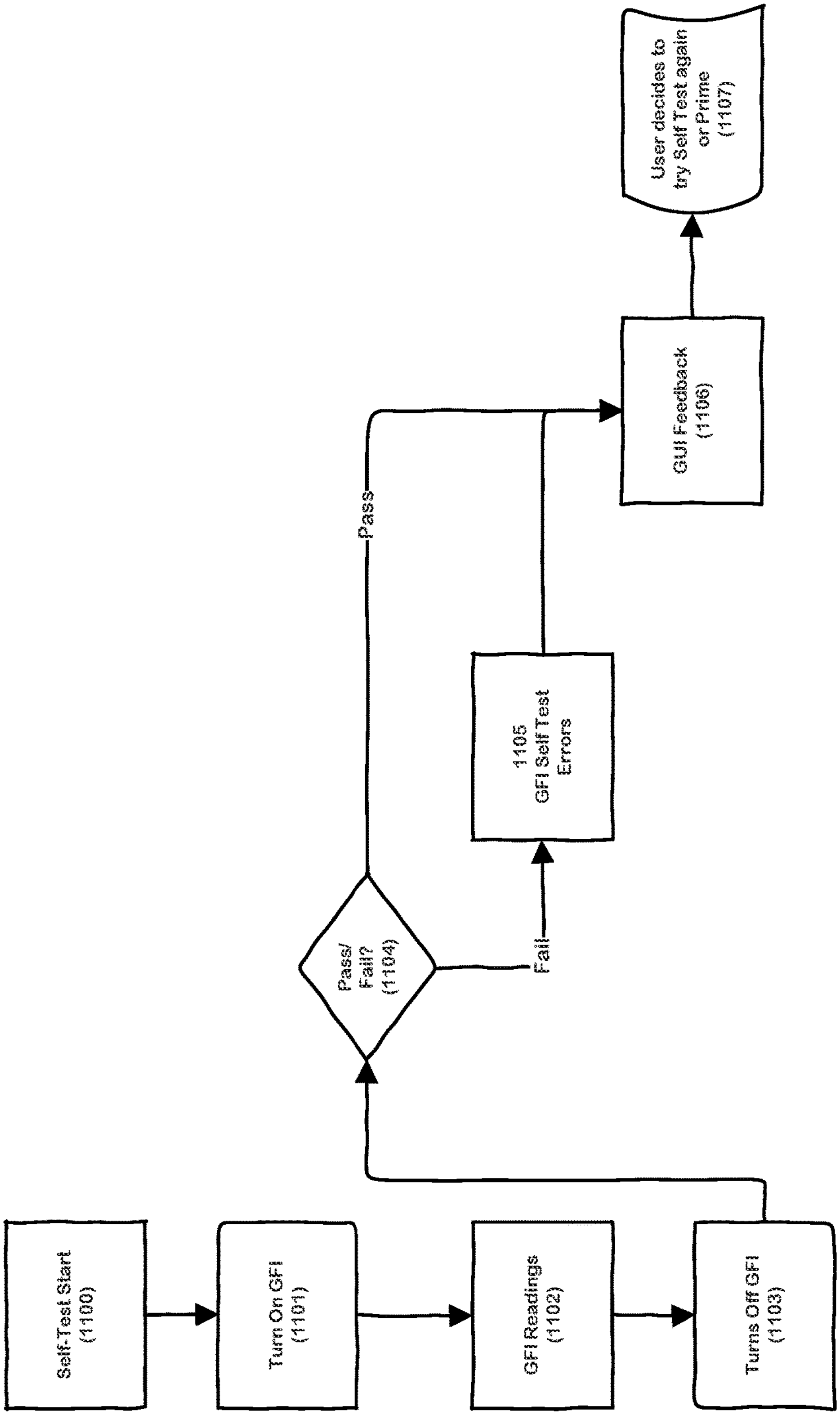
FIGS. 11*a* and 11*b* are flow diagrams illustrating aspects of the embodiments.
Figure 11B:
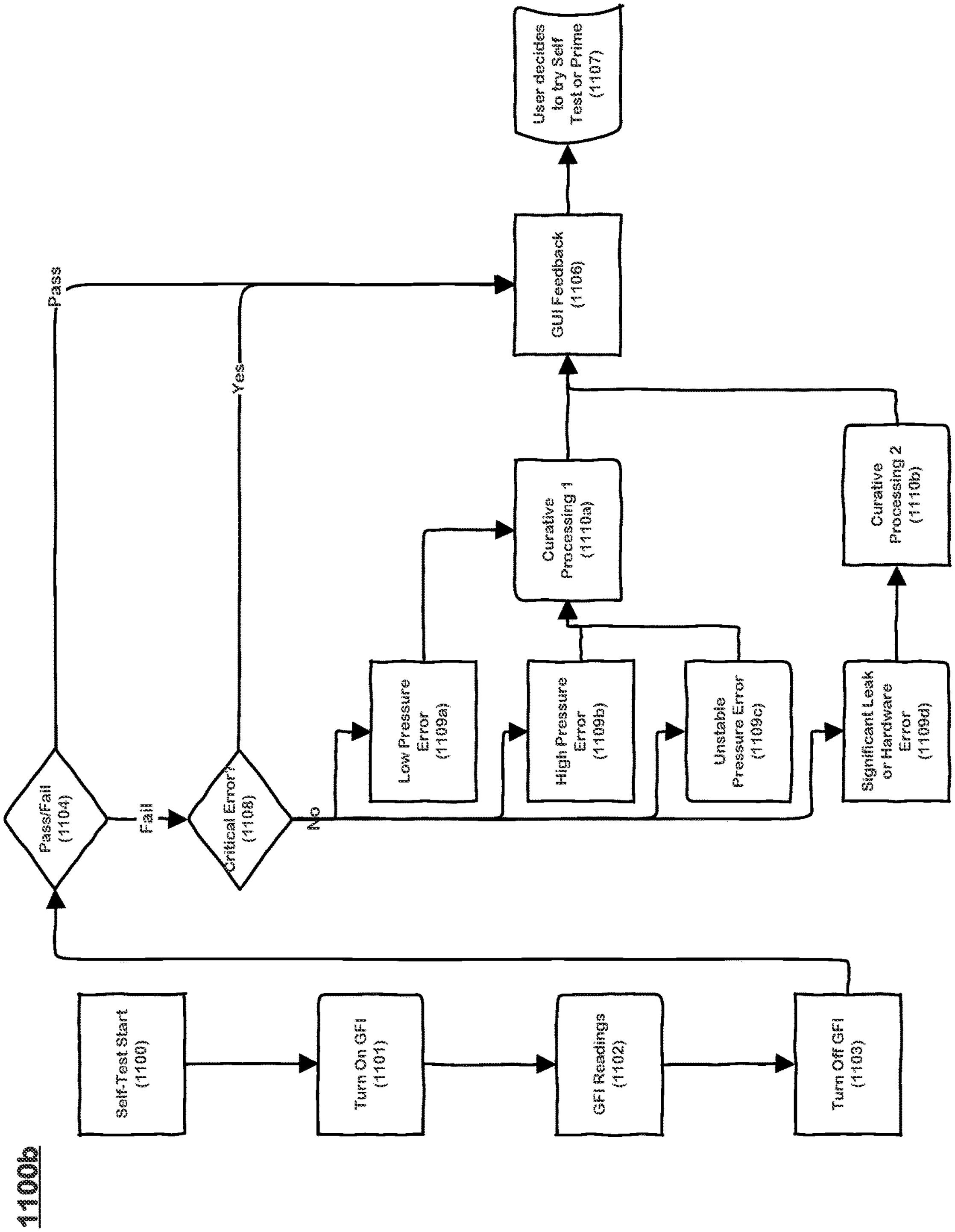

More specifically, and as illustrated in the flow diagrams of FIGS. 11*a* and 11*b*, a first algorithm (1100*a*) and second algorithm (1100*b*), respectively, comprising a self-test are shown that assess the availability of the gas infusion discussed throughout. FIGS. 11*a* and 11*b* describes the GFI algorithm during self-test (1100*a* and 1100*b*). FIG. 11*a* describes the current implementation of self-test with GFI while FIG. 11*b* describes an alternate implementation to the self-test with GFI algorithm.

In FIG. 11*a*, a first embodiment of a self-test algorithm 1100*a* is shown. The self-test algorithm 1100*a* may include a plurality of algorithmic steps, such as may be initiated by the instrument host, either automatically upon occurrence of a trigger or responsive to entries to the GUI 700 by a user, this describes the current implementation of the self-test GFI algorithm (1100*a*). The self-test algorithm 1100*a* begins at self-test start 1100, which may occur either at system bootup or when a user manually requests it through the GUI 700. Once started, the system turns on the GFI at step 1101 and the system waits for the GFI module located in console 210 to initialize and stabilize, i.e., finish the boot up protocol. This may typically occur in about 600 milliseconds, for example. The system then proceeds to loop through a series of GFI readings at step 1102, which may be a firmware loop that runs any number of times within a predetermined period of time to collect the desired readings, e.g., the firmware may loop 150 times for about e.g, for 600 milliseconds (ms). The GFI readings at step 1102 may include one or more of the following: includes the pressure readings, valve overcurrent readings, and/or regulator overcurrent readings. and the system then proceeds to turn off the GFI at step 1103 and then the system checks the GFI readings at step 1102 to determine whether the readings pass or fail at step 1104, i.e., are within or outside a desired and/or pre-selected range. As a non-limiting example, a desired or pre-determined GFI pressure reading range may be between of 10 mmHg and 30 mmHg. If the GFI self-test passes at step 1104, the system sends the user GUI feedback 1106 to the GUI 700 to inform the user and then the user may decide to prime the system at step 1107 to continue.

In an embodiment, if the GFI readings 1102 fall outside the desired and/or pre-determined GFI pressure range, the self-test fails, and the GFI self-test errors 1105 are provided to a user as GUI feedback 1106. As a non-limiting example, if the GFI pressure readings are not within between 10 mmHg and 35 mmHg, the self-test fails. In an embodiment, the self-test may also check for valve and/or regulator overcurrent at GFI readings step 1102 to determine whether each component is within its specified/desired range and determine if those readings pass or fail at step 1104. If readings are outside of the specified/desired range, the readings are marked as unstable and the system proceeds via the failed path. The system may also check for hardware failure and flags error, e.g., reservoir leakage, at GFI readings 1102. The system then provides the GFI self-test errors 1105 as GUI feedback 1106 to the user via GUI 700 and the user may decide to run the self-test again or try prime to see if the error is corrected at step 1107. If the GFI self-test fails, the system sends the GUI feedback 1106 to GUI 700 to inform the user that the GFI is not available, and the user may decide to prime the system to continue at step 1107. In an embodiment, the user may decide to run the system without GFI and use the standard gravity fed method.

In FIG. 11*b*, a second embodiment of a self-test algorithm 1100*b* is shown. The self-test algorithm 1100*b* may include a plurality of algorithmic steps, such as may be initiated by the instrument host, either automatically upon occurrence of a trigger or responsive to entries to the GUI 700 by a user. The self-test algorithm 1100*b* begins the same as self-test algorithm 1100*a* with the same steps 1100, 1101, 1102, and 1103 described above. Also similar to self-test algorithm 1100*a*, the system checks the GFI readings at step 1102 to determine whether the readings pass or fail at step 1104, i.e., are within or outside a desired and/or pre-determined range. As a non-limiting example, a desired or pre-determined GFI pressure range may be between 10 mmHg and 30 mmHg, but may vary depending on the many factors, including the type of system. If the GFI self-test passes at step 1104, the system sends the GUI feedback 1106 to the GUI 700 to inform the user and then the user may decide to prime the system at step 1107 to continue.

In an embodiment, if the GFI readings 1102 fail indicating one or more errors, i.e., the readings fall outside the desired and/or pre-determined GFI pressure range, the system proceeds to determine if the errors are critical errors at step 1108. A critical error could be any significant or unrecoverable error, such as a dangerous condition, e.g., exceedingly high pressure and/or a hardware failure. If the error is determined to be critical at step 1108, the system will send GUI feedback 1106 to inform the user that GFI is not available, and user may decide to try self-test again or try prime at step 1107.

In an embodiment, if there is no critical error at step 1108, the system proceeds to correct the non-critical error based on the type of non-critical error detected. For example, the system may check for GFI pressure readings that are outside of the desired or pre-determined valid range and trigger either a low pressure error (1109*a*) (which may be an out of range low pressure) and/or a high pressure error (1109*b*) (which may be an out of range high pressure)), and/or checks for valve and/or regulator overcurrent to determine whether each component is outside of the desired or pre-determined range resulting in an unstable pressure error (1109*c*). For errors 1109*a*, 1109*b*, and 1109*c*, the system proceeds to curative processing 1 (1110*a*) where it adjusts the pressure to attempt to get the GFI pressure readings back within the desired or pre-determined range. The system then determines if the curative processing 1 step 1110*a* successfully corrected the one or more errors and sends GUI feedback 1106 to inform the user of the results of the GFI self-test. If the curative processing 1 (1110*a*) is successful, the user may decide to proceed to prime (1107). If the curative processing 1 (1110*a*) is not successful, the user may decide to try self-test again or proceed to prime to see if the errors can be corrected (1107).

In an embodiment, the system may also check for a significant leak and/or hardware failure, e.g., reservoir leakage, and trigger a significant leak or hardware error (1109*d*). The system then proceeds to curative processing 2 (1100*b*) where the system performs an auto-reboot of the fluidics module and may perform a self-test on the fluidics module to reset the fluidics module back to an initialized state (e.g., the state after the initial boot up of the system or ready state). The system then proceeds to send GUI feedback 1106 to the user via GUI 700 to recommend performing the self-test again (1107).

In an embodiment, the curative processing 1 (1110*a*) and 2 (1110*b*) may continue during the self-test as needed whenever the error conditions are detected to attempt to correct the detected errors.

Figure 12A:
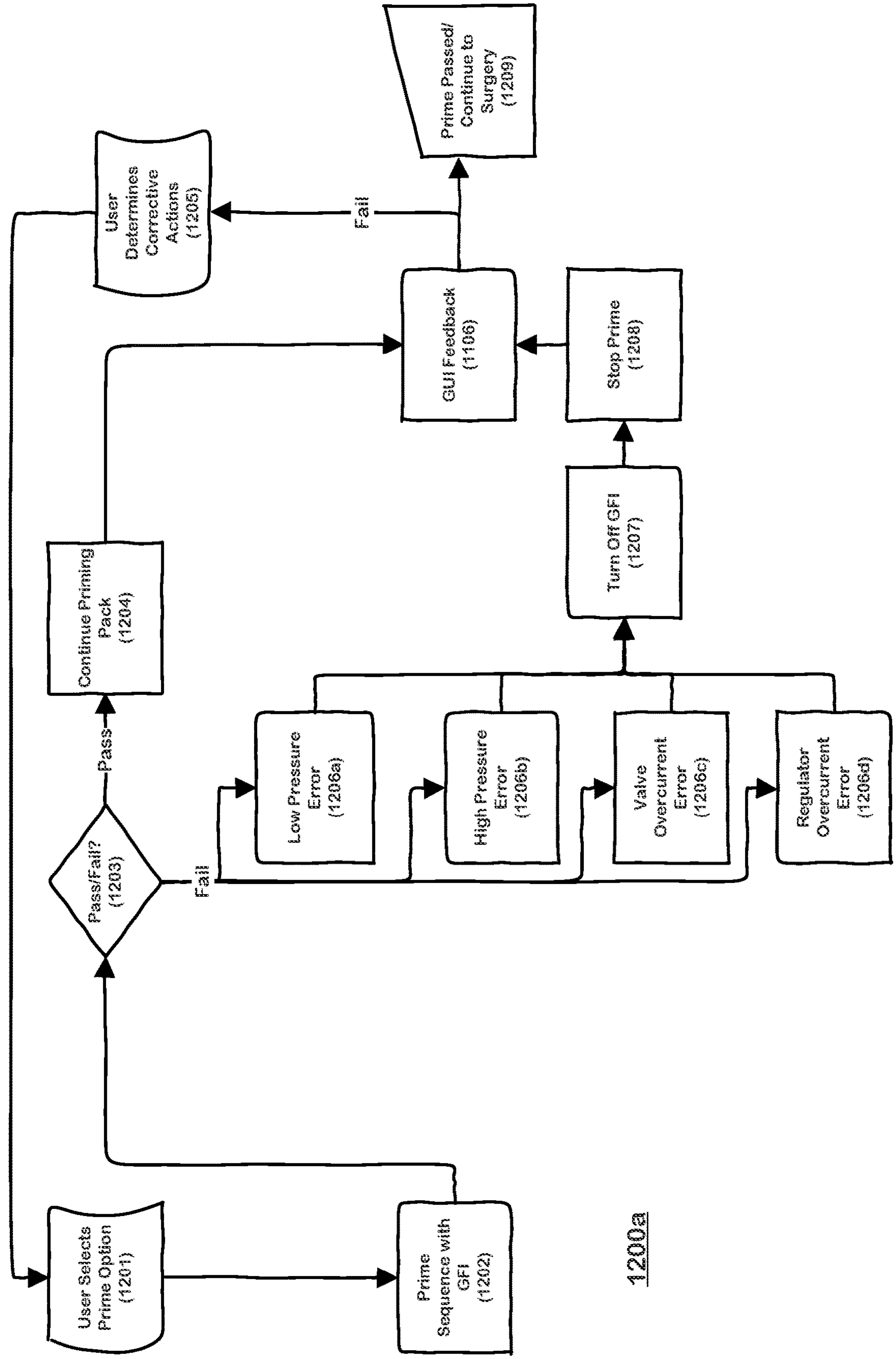
FIGS. 12*a* and 12*b* are flow diagrams illustrating aspects of the embodiments.
Figure 12B:
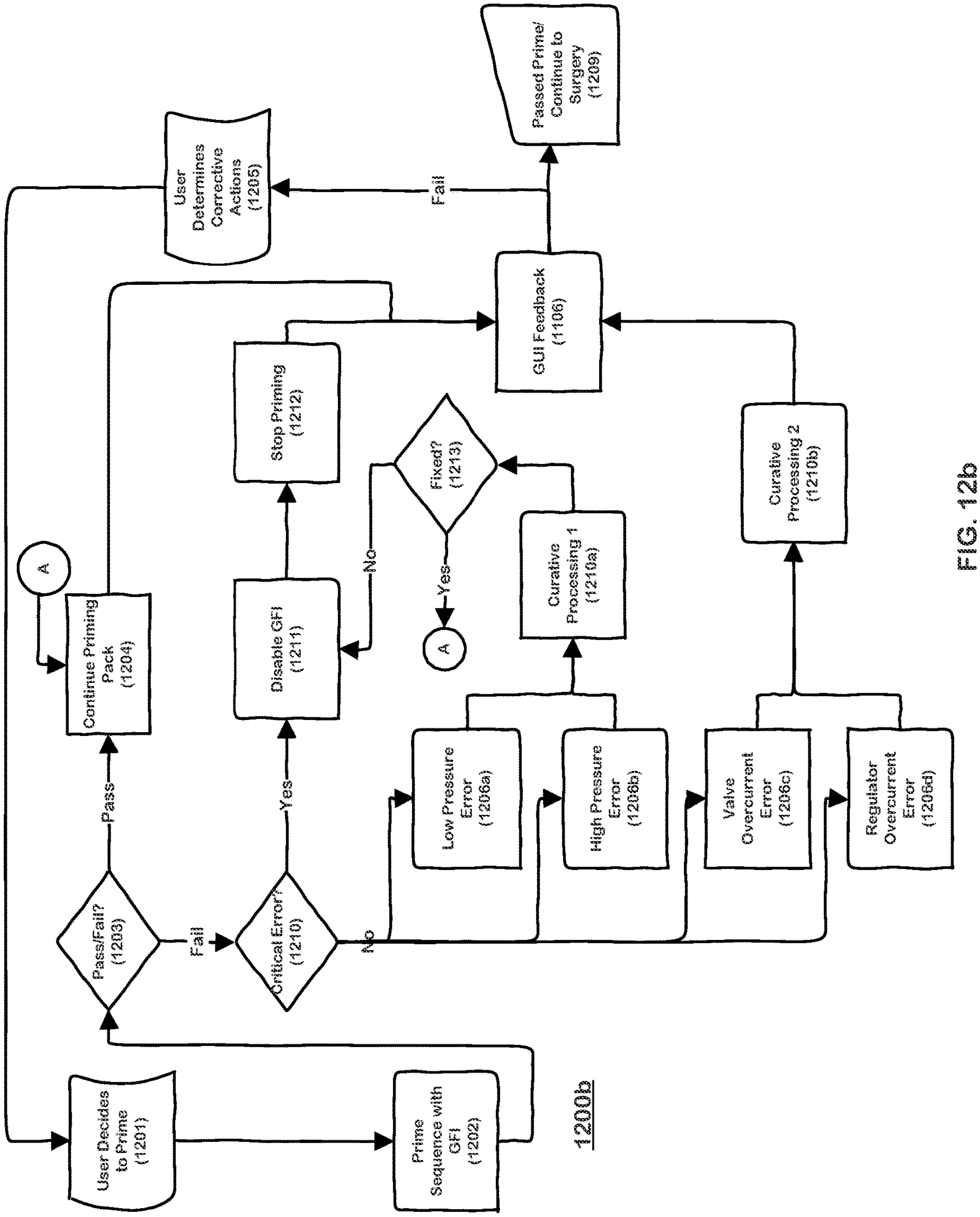

FIGS. 12*a* and 12*b* describes GFI priming algorithms 1200*a* and 1200*b*. These GFI priming algorithms may occur regularly, such as upon each use of the phacoemulsification console (e.g., each cataract procedure), upon each replacement of the pack or other hardware, and/or may occur with varying frequency depending upon the circumstances. The frequency of and the circumstances for priming may be detailed to, or may occur responsive to instructions from, the user using the GUI 700 (as is illustrated in the exemplary embodiment of FIG. 8). That is, the priming/tuning process may indicate the process steps on GUI 700, such as may include the insertion of a pack, the filling of tubing with fluid, the performing of a vacuum check, and the testing and characterization of the handpiece, such as in addition to priming and testing of the gas infusion hardware as discussed throughout. The embodiments described herein, provide for a more efficient priming when using GFI or a combination of GFI and gravity fed methods.

In FIG. 12*a*, a first embodiment of a GFI priming algorithm 1200*a* is shown. The GFI priming algorithm 1200*a* may include a plurality of algorithmic steps, such as may be initiated by the instrument host, either automatically upon occurrence of a trigger or responsive to entries to the GUI 700 by a user. The GFI priming algorithm 1200*a* begins when a user inserts pack 400 into console 210 and selects the prime option on the GUI 700 of the phacoemulsification system at step 1201 with the GFI enabled. Once prime has been selected at step 1201, the system performs the prime sequence with GFI at step 1202. During the prime sequence with GFI 1202, the system performs a series of GFI tests/readings, which may include pressure readings, valve overcurrent readings, regulator overcurrent readings (e.g., dump valve, GFI valve and regulator), and compares the readings to desired and/or pre-determined ranges (or criteria) for each of the readings to determine whether the readings pass or fail at step 1203. If the readings are within the desired and/or pre-determined ranges, the prime sequence passes and the system proceeds to continue priming the pack 400 at step 1204, which includes all other typical priming steps that occurs without GFI known in the art, e.g., checking different pressures and settings to make sure the fluidics function correctly. At this point, continue priming pack 1204 could fail due to non-GFI related issues. In this scenario, any failure is identified with an error number that is displayed on the GUI, which includes GFI related errors and regular prime errors (e.g., low head height pressure (bottle too low), hardware failure (peristaltic and/or venturi pump failure), etc.).

The system then sends the results of the priming with GFI to the user as GUI feedback 1106. Finally, the system may continue to surgery at step 1209 if successful. If continue priming pack step 1204 fails, the user is notified of the failure as GUI feedback 1106 and the user may then determine how to proceed to correct any failure at step 1205 which may include taking one or more system recommended corrective steps, e.g., checking the connection of the GFI tubing, eject and reinsert the pack, or replacing the pack with a new pack. The user then may decide to prime again at step 1201 to see if the error has been corrected.

In an embodiment, if the GFI tests/readings of prime sequence with GFI 1202 fail because the GFI tests/readings fall outside of the desired or pre-determined ranges (passing criteria) resulting in errors, the system proceeds to process the errors via the "fail" pathway. In an embodiment, the type of errors may include a low pressure error (which may be an out of range low pressure) (1206*a*), a high pressure error (which may be an out of range high pressure) (1206*b*), a valve overcurrent error (1206*c*), and/or a regulator overcurrent error (1206*d*). If one or more of the errors 1206*a*, 1206*b*, 1206*c*, and 1206*d* occur, the system proceeds to turn off GFI at step 1207 and stop the prime at step 1208. Next, the system provides the error(s) as GUI feedback 1106 to the user via GUI 700 and the user determines how to proceed to correct the error(s) at step 1205, which may include taking one or more system recommended corrective steps, e.g., checking the GFI tubing connections or replace the pack with a new pack. The user may then decide to prime again at step 1201 to see if the error has been corrected.

In FIG. 12*b*, a second embodiment of a of a GFI priming algorithm 1200*b* is shown. The GFI priming algorithm 1200*b* may include a plurality of algorithmic steps, such as may be initiated by the instrument host, either automatically upon occurrence of a trigger or responsive to entries to the GUI 700 by a user. The GFI priming algorithm 1200*b* begins as described above for GFI priming algorithm 1200*a* with respect to steps 1201, 1202, and 1203.

Similarly, if the readings are within the desired and/or pre-determined ranges, the prime sequence with GFI passes at step 1203 and the system proceeds to continue priming the pack 400 at step 1204. The system then sends the results of the priming with GFI to the user as GUI feedback 1106. Finally, the system may continue to surgery at step 1209 if successful. If continue priming packs step 1204 fails, the user is notified of the failure as GUI feedback 1106 and the user may then determine how to proceed to correct any failure at step 1205 which may include taking one or more system recommended corrective steps, e.g., checking the connection of the GFI tubing, ejecting and reinserting the pack, or replacing the pack with a new pack. The user then may decide to prime again at step 1201 to see if the error has been corrected.

In an embodiment, if the GFI tests/readings of prime sequence with GFI 1202 fail because the GFI tests/readings fall outside of the desired or pre-determined ranges (passing criteria) resulting in errors, the system proceeds to check if it is a critical error at step 1210). A critical error could be any significant or unrecoverable error, such as a dangerous condition, e.g, exceedingly high pressure and/or a hardware failure. If the system determines there is a critical error, the system will disable GFI at step 1211 and stop priming (1212). The system then provides the GUI feedback 1106 to the user via GUI 700 and the user determines how to proceed to correct the error at step 1205, which may include checking and reconnecting GFI tubing or replacing the pack with a new pack. The user may then decide to prime again at step 1201 to see if the error has been corrected.

In an embodiment, if there is no critical error at step 1210, the system proceeds to try to correct the non-critical error(s) based on the type of non-critical error(s) to enable priming to continue. In an embodiment, the type of errors may include a low pressure error (which may be an out of range low pressure) (1206*a*), a high pressure error (which may be an out of range high pressure) (1206*b*), a valve overcurrent error (1206*c*), and/or a regulator overcurrent error (1206*d*). If one or more of the errors 1206*a* or 1206*b* occur, the system proceeds to curative processing 1 (1210*a*) where the system adjusts the pressure to try to get the GFI pressure back within the desired or pre-determined range. The system then proceeds to determine if the curative processing 1 (1210*a*) fixed the error at step 1213. If curative processing 1 (1210*a*) is able to correct the error, the system may continue with priming the pack at step 1204 and send the priming with GFI results as GUI feedback 1106 to the user via GUI 700. Based on the priming with GFI results, the system may continue to surgery at step 1209 if successful. If continue priming pack step 1204 fails, the user is notified of the failure as GUI feedback 1106 and the user may determine how to proceed to correct any failure at step 1205, which may include taking one or more system recommended corrective steps, e.g., checking the GFI tubing, ejecting and reinserting the pack, or replacing the pack with a new pack. The user then may decide to prime again at step 1201 to see if the error has been corrected.

In an embodiment, if curative processing 1 (1210*a*) is not fixed at step 1213, then the system will disable GFI at step 1211 and stop priming at step 1212. The system then provides GUI feedback 1106 to the user via GUI 700 and the user determines how to proceed to correct the error at step 1205, which may include taking one or more system recommended corrective steps and/or reprime and tune.

In an embodiment, if one or more of errors 1206*c* or 1206*d* occur the system will attempt curative processing 2 (1210*b*) where the system performs an auto-reboot of the fluidics module). The auto-reboot may include performing a self-test on the fluidics module to reset the fluidics module back to an initialized state (e.g., the state after the initial boot up of the system or ready state). The system will then send GUI feedback 1106 to the user via GUI 700 and the user may then determine how to proceed to correct any failure (or error) that still exists at step 1205, which may include taking one or more system recommended corrective steps, e.g., re-prime and tune. If at this point the error is corrected, the system may continue to surgery step 1209. In an embodiment, these algorithm loops may continue as long as the user continues to encounter errors during priming.

In any of the GFI priming algorithm embodiments described herein, to shorten the timing and improve the performance of priming with GFI at the start of priming step 1201, the IV pole height may be increased in embodiments including an IV pole, such as to a height greater than 75 cm. The gas infusion may add pressure of 15 cm to 45 cm of height, by way of non-limiting example, to the pressure commensurate with the actual height of the IV pole, and this, in conjunction with an increased height of the fluid source, increases the fluid flow in a controlled manner to fill the pack tubing with fluid at a much faster priming rate than current methods allow. In addition, this priming methodology reduces possible failures from bubbles building up in the tubing, due to the increased flow of fluid through the tubing.

In an embodiment, the final prime sequence effectuated and provided as GUI feedback 1106 to GUI 700 should be at the ultimate height of the IV Pole height plus the "virtual height" added through the use of the GFI. Of course, if the IV pole is not lowered for the final priming sequence, the algorithms may be updated to account for the difference in height by modifying the acceptable data criteria with updated offsets to complete the priming and allow for surgery to begin. Not changing the IV pole height to complete priming can also further reduce the time that priming takes. Simply put, the disclosed algorithms calculate based on an actual IV pole height of 75 cm, and thus having the IV pole at that actual height simplifies the processing and updating of offsets. In an embodiment, the physical maximum IV pole height available may be 106 cm and with the addition of an equivalent flow pressure of between 15 cm to 45 cm via the gas infusion (GFI) the maximum IV pole height available may be a theoretical 151 cm.

In other embodiments, other variations in the priming may occur, such as dependent upon whether the irrigation source is sensed, or indicated to the GUI, as a plastic bag or a glass bottle. In this example, pressurizing the plastic bag takes more time than the bottle because of expansion of the plastic materials. To address this, the GFI may pressurize the plastic bag at a higher pressure than it would a bottle, and then may reduce the pressure after the initial priming sequence.

Figure 13A:
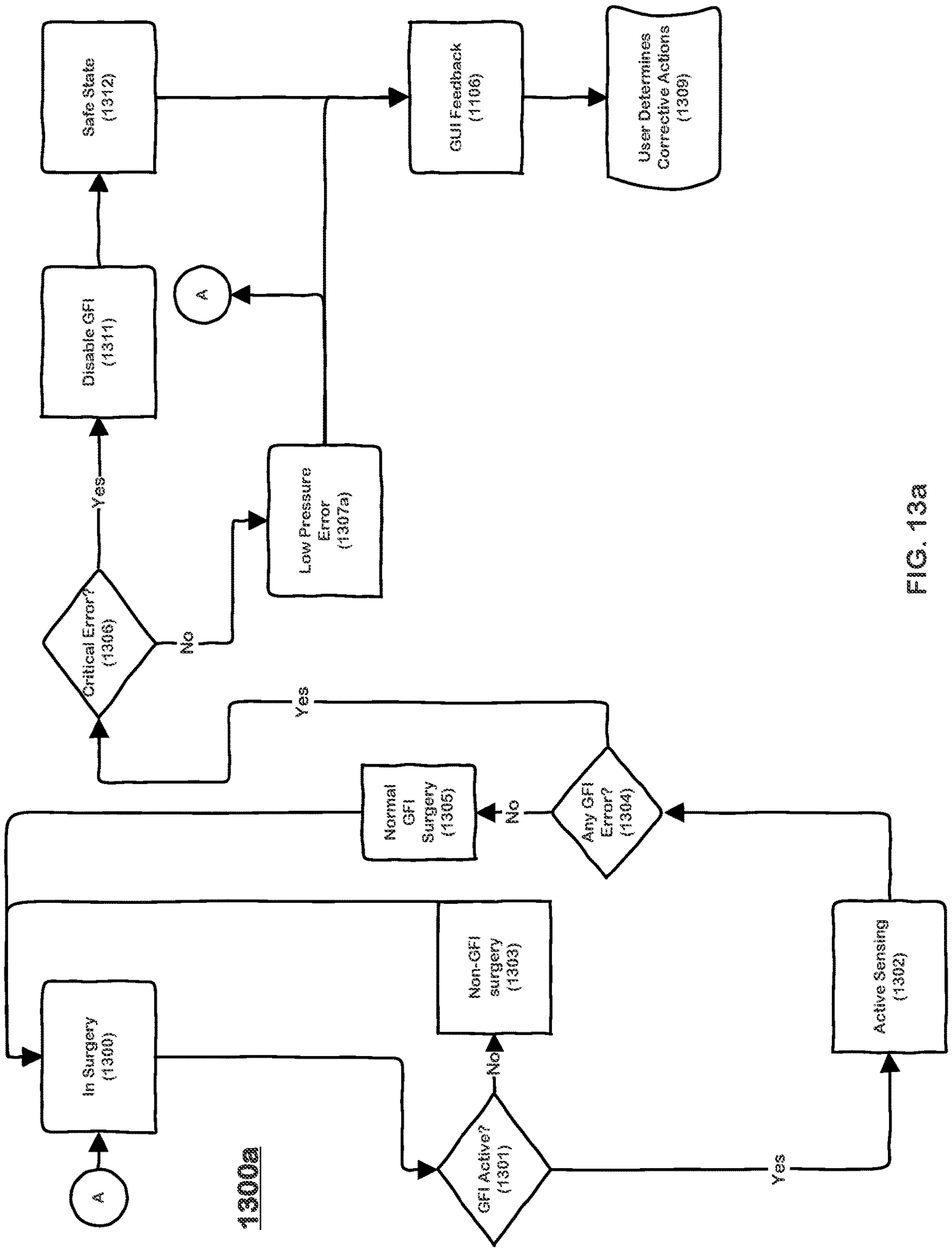
FIGS. 13*a* and 13*b* are flow diagrams illustrating aspects of the embodiments.
Figure 13B:
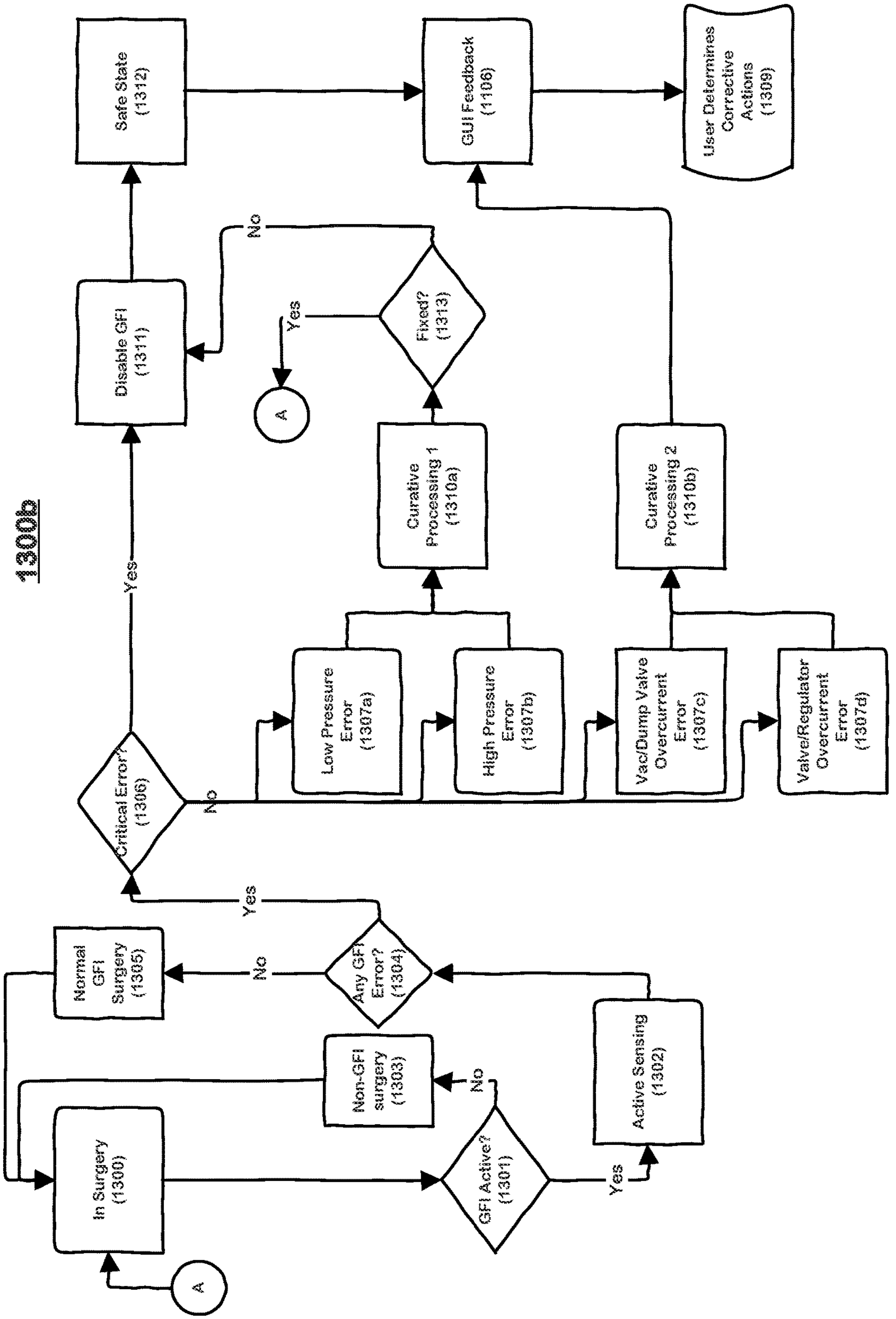

FIGS. 13*a* and 13*b* describe GFI algorithms during surgery (1300*a* and 1300*b*). The GFI algorithms during surgery 1300*a* and 1300*b* may include a plurality of algorithmic steps, such as may be initiated by the instrument host, either automatically upon occurrence of a trigger or responsive to entries to the GUI 700 by a user. In the embodiments described herein, the GFI may be actively monitored during surgery, such a via sampling, user feedback, and active sensing.

In FIG. 13*a*, a first embodiment of GFI during surgery algorithm (1300*a* is shown). Once in surgery (1300) (i.e., the process of cataract removal, including when the footpedal is activated), the GFI algorithm during surgery 1300*a* proceeds to check if the GFI is active at step 1301. If GFI is not active, the system proceeds to a non-GFI surgery algorithm (1303). In an embodiment, this loop may continue throughout surgery and the system continues to check if the GFI is active. In the scenario where the GFI is active at step 1301, the system performs active sensing at step 1302 and continuously checks for any GFI errors at step 1304 in surgery mode. If there are no GFI errors, the system proceeds with normal GFI surgery at step 1305. This loop continues throughout surgery and the system continuously checks for GFI errors. If a GFI error is encountered at step 1304, the system proceeds to check if it is a critical error at step 1306. A critical error may be any significant or unrecoverable error, such a dangerous condition, e.g, exceedingly high pressure and/or a hardware failure. If there is a critical error at step 1306, the system will disable GFI at step 1311 and enter a safe state at step 1312. The system then provides the GUI feedback 1106 to the user via GUI 700 and the user may determine how to proceed to correct the error at step 1309, which may include taking one or more system recommended corrective steps, reprime and tune to continue with surgery, and/or to continue surgery without GFI where the user disconnects the GFI tubing and adjusts the IV pole to compensate for the GFI pressure to reach the targeted pressure setting. In an embodiment, if at any point during surgery the user decides to use GFI and enables it, the system switches to use active sensing (1302) and proceeds via the options of this loop. In an embodiment, when the system enters a safe state at step 1312, the IH prevents surgery and keeps the irrigation valve open and/or allows the foot pedal to control opening/closing of the irrigation valve until the system is no longer in the safe state.

In an embodiment, if there is no critical error at step 1306, the system proceeds to monitoring the non-critical error(s) to enable surgery to continue. For example, a non-critical error may be a small leak in the gas feed line resulting in low pressure error 1307*a*. In this example, a low pressure error 1307*a* may be when the pressure detected during active sensing 1302 is less than a desired or pre-determined pressure or pressure range, e.g., less than 17 mmHg. The system proceeds to provide GUI feedback 1106 to the user and the user determines how to proceed to correct the low pressure error 1307*a*, which may include taking one or more system recommended corrective steps, including checking the GFI tubing connections, adjusting the height of the IV pole if proceeding without GFI, and/or repriming to continue with surgery. This loop continues to check if the non-critical error, e.g., low pressure error 1307*a*, has been corrected (e.g., pressure readings return within range a desired or pre-determined range, such as between 17 mmHg and 27 mmHg) by returning back to the in surgery step 1300. Next, the system will cycle through step 1301 and continue based on by result of each step. For example, if the GFI is active and the error has been corrected, the system proceeds with normal GFI surgery at step 1305.

In FIG. 13*b*, a second embodiment of a GFI during surgery algorithm 1300*b* is shown. This algorithm embodiment includes curative implementations by the system. The GFI during algorithm 1300*b* begins as described above for GFI priming algorithm 1200*a* with respect to steps 1300, 1301, 1302, 1303, 1304, and 1305. In an embodiment, if a GFI error is encountered at step 1304, the system proceeds to check if it is a critical error at step 1306. A critical error could be any significant or unrecoverable error, such as a dangerous condition, e.g., exceedingly high pressure and/or a hardware failure. The system will next disable the GFI at step 1311 and enter a safe state at step 1312. The system then provides the GUI feedback 1106 to the user and the user determines how to proceed to correct the error at step 1309, which may include taking one or more system recommended corrective steps, reprime and tune to continue with surgery, and/or continue surgery without GFI where the user disconnects the GFI tubing and adjusts the IV pole to compensate for the GFI pressure to reach the desired or pre-determined pressure setting. In an embodiment, when the system enters a safe state at step 1312, the IH prevents surgery and keeps the irrigation valve open and/or allows the foot pedal to control opening/closing of the irrigation valve until the system is no longer in the safe state.

In an embodiment, if there is no critical error at 1306, the system proceeds to correct the non-critical error(s) based on the type of non-critical error(s) to enable surgery to continue. In an embodiment, the type of errors may include a low pressure error (1307*a*) (which may be an out of range low pressure), a high pressure error (1307*b*) (which may be an out of range high pressure), a vacuum or dump valve overcurrent error (1307*c*), and/or a valve or regulator overcurrent error (1307*d*). If one or more of the errors 1307*a* or 1307*b* occur, the system proceeds to curative processing 1 (1310*a*) where the system adjusts the pressure to try to get the GFI pressure back within the desired or pre-determined range. The system then proceeds to determine if the curative processing 1 (1310*a*) fixed the error at step 1313. If curative processing 1 (1310*a*) is able to correct the error, the system can continue with surgery (1300). In an embodiment, this loop may continue to run while in surgery to detect errors, if any, and respond accordingly based on one of the algorithms described herein. If curative processing 1 (1310*a*) is unable to correct the error at step 1313, then the system will disable the GFI at step 1311 and enter a safe state at step 1312. The system then provides GUI feedback 1106 to the user and the user determines how to proceed to correct the error at step 1309, which may include taking one or more system recommended corrective steps, reprime and tune to continue with the surgery, and/or continue the surgery without GFI. In an embodiment, if other types of non-critical errors such as vacuum or dump valve overcurrent error (1307*c*) and/or valve or regulator overcurrent error (1307*d*) are detected, the system will attempt curative processing 2 (1310*b*) where the system performs an auto-reboot of the fluidics module. The auto-reboot may include performing a self-test on the fluidics module to reset the module back to an initialized state. The system will provide GUI feedback 1106 to the user and the user will determine the corrective action at step 1309, which may include re-prime and tune. If at this point the error has been corrected, surgery may continue at step 1300. In an embodiment, these loops will continue as long as the user continues to be in surgery mode.

In an embodiment, during surgical operation, the system may provide an editable (via the GUI 700) GFI target setting, by which the user may define the amount of pressure to add to the irrigation flow via the GFI. These GFI settings may have pre-defined choices correspondent to IV pole height ranges, as discussed throughout, such as of low (11 mmHg), medium (22 mmHg), and high (33 mmHg), or to a customizable value, such as between 11-33 mmHg (equivalent to about 15 to about 45 cm of IV pole height). The selected pressure from the GUI is sent to the instrument host to control the amount of pressure stemming from the infusion source.

In an embodiment, various surgical submodes may have varying GFI ranges available via the GUI 700, or via a preprogrammed surgical format. This infused pressure may, in each mode, simply provide additional irrigation flow over and above that available due to the IV pole height, and/or may provide curative pressures to maintain safe operation and/or correct any hardware or software errors during surgery.

Figure 14:
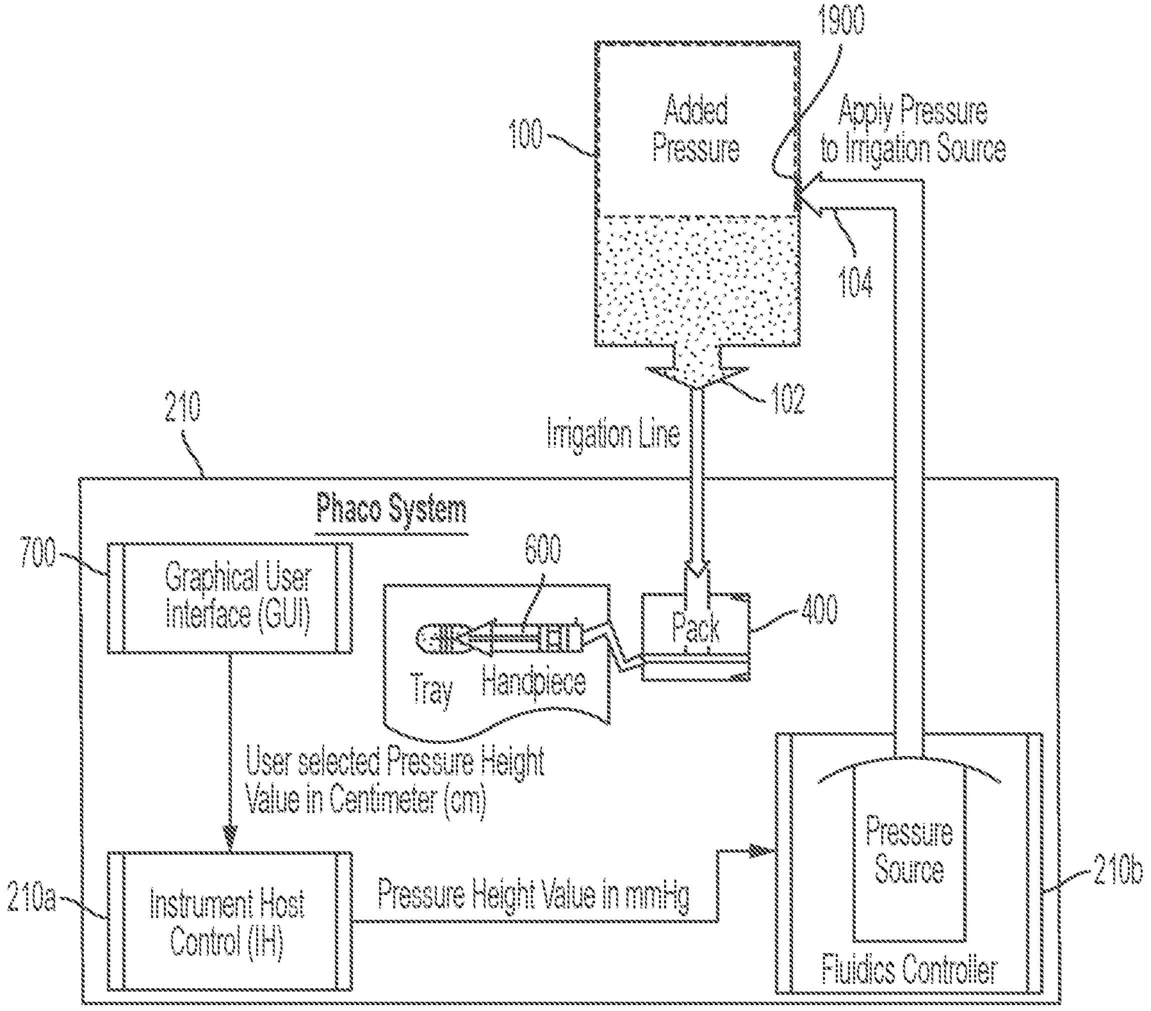
FIG. 14 is an illustration of a surgical system.

A particular application of the foregoing algorithms to the disclosed gas infusion in a phacoemulsification system is illustrated in FIG. 14. As shown, the GUI 700 may present to a user an option to select a pressure equivalent to a particular height of an IV pole. Such available selections may be provided to the user as pressures, or height equivalents, by way of example. These selections may be provided using the algorithms discussed above.

In the illustration, available GUI options selectable by the user may include low (such as 15 cm), medium (such as 30 cm) or high (such as 45 cm) equivalent IV pole height. These options may be equated by the instrument host 210*a*, such as using the algorithms discussed above, to 11, 22, or 33 mmHg for the pressure on the irrigation source 100.

The instrument host 210*a*, i.e., the processor of the phacoemulsification console 210, may receive and convert this selection from the GUI 700. The instrument host 210*a* may then execute a series of control signals to the fluidics controller 210*b* of the console 210 in order to affect the desired/selected irrigation flow.

In short, the fluidics control may outlet gas, as discussed herein, to the gas infusion port 104 so as to effectuate the desired pressure on the irrigation source 100. As illustrated by comparison with the exemplary embodiment of FIG. 4, the type and location of the gas infusion 104 may vary in relation to the irrigation source 100. This pressure affects the irrigation flow outwardly from port 102 of the irrigation source 100.

In an embodiment, an automated or manual pressure relief valve or valves 1900 may be included, such as in the event a pressurization error occurs during self-test, priming, or surgery, as discussed above. It will be appreciated that the type and location of valve 1900 in FIG. 14 is exemplary only, and that any type of valve 1900 may be used, and at any location on the irrigation source, along the gas infusion or irrigation lines, or within the console 210. Additionally, the term "valve" 1900, as used herein, is intended to include any type of pressurization relief systems or devices, including algorithmic actuation by the instrument host 210*a*. In an embodiment, pressure relief may occur by turning off pressurization and running the irrigation from the bottle to relieve the remaining pressure built up inside the bottle for a pre-defined amount of time.

The irrigation flow proceeds to the pack 400, which provides irrigation to the handpiece 600. The handpiece 600 then provides the irrigation to the eye to optimize performance of the phacoemulsification surgery.

Although the exemplary embodiments may be discussed herein with respect to a phacoemulsification system, those skilled in the art will appreciate that the disclosed apparatus, system, and method may be applied to any medical, pharmaceutical, or surgical system which requires expedited and refined adjustments in the head pressure on a surgical fluid. Moreover, the embodiments allow for the liquid and closed surgical system to remain sterile, at least in that no pump is needed for insertion between a liquid source and an application.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. A surgical system, comprising:

a spike suitable for insertion into a fluid reservoir containing a surgical fluid and a gas pressure pocket, wherein the spike comprises a first port configured to provide the surgical fluid from the fluid reservoir to a surgical pack associated with the surgical system and a second port configured to provide pressurized gas from a pressurized gas source to the fluid reservoir;

a controller, wherein the controller is configured to, during a self-test for determining an availability of the pressurized gas source prior to a surgical procedure:

obtain one or more pressure readings associated with the pressurized gas;

obtain one or more overcurrent readings associated with a valve or a regulator;

enable an operation of the pressurized gas source if the one or more pressure readings associated with the pressurized gas are within a first predetermined range and the one or more overcurrent readings are within a second pre-determined range;

disable the operation of the pressurized gas source if the one or more pressure readings associated with the pressurized gas are an amount outside of the first predetermined range that causes a critical error or the one or more overcurrent readings are an amount outside of the second pre-determined range that causes the critical error; and iteratively modify the surgical system, if the one or more pressure readings associated with the pressurized gas are between the first pre-determined range and the amount outside of the first pre-determined range that causes the critical error, until one or more subsequent readings associated with the pressurized gas are brought within the first pre-determined range.

2. The surgical system of claim 1, wherein the fluid reservoir comprises a bottle or a bag.

3. The surgical system of claim 1, wherein the surgical fluid comprises a balanced salt solution.

4. The surgical system of claim 1, wherein the surgical fluid fluidically couples the surgical pack to a phacoemulsification handpiece.

5. The surgical system of claim 1, wherein the pressurized gas source infuses air into the gas pressure pocket of the fluid reservoir.

6. The surgical system of claim 1, wherein the one or more pressure readings associated with the pressurized gas are within the first pre-determined range when the one or more pressure readings are between 10 mmHg and 30 mmHg.

7. The surgical system of claim 1, the controller configured to take the one or more pressure readings associated with the pressurized gas during a priming sequence.

8. The surgical system of claim 7, the controller configured to notify a user via a graphical user interface (GUI) by indicating a result of the priming sequence.

9. The surgical system of claim 1, said controller configured to notify a user via a graphical user interface (GUI) if the one or more pressure readings associated with the pressurized gas are outside of the first pre-determined range.

10. The surgical system of claim 1, said controller further configured to, in response to the one or more subsequent readings associated with the pressurized gas being brought within the first pre-determined range, execute one or more steps of a system prime sequence while the operation of the pressurized gas source is enabled.

11. The surgical system of claim 10, wherein the fluid reservoir is a pole-mounted fluid reservoir, and wherein said controller is further configured to, prior to obtaining the one or more pressure readings associated with the pressurized gas, increase a flow rate of the surgical fluid by increasing a height of the pole-mounted fluid reservoir.

12. The surgical system of claim 10, wherein the fluid reservoir is a pole-mounted fluid reservoir, wherein the controller is further configured to determine a virtual height of the pole-mounted fluid reservoir that accounts for a pressure provided by the pressurized gas source and an actual height of the mounted fluid reservoir, and wherein the controller is further configured to execute, using the virtual height of the pole-mounted fluid reservoir, the one or more steps of the system prime sequence while the operation of the pressurized gas source is enabled.

13. The surgical system of claim 1, the controller further configured to:

determine, based on the one or more pressure readings or the one or more overcurrent readings, a presence of a leak or a hardware error; and in response to determining the presence of the leak or the hardware error, carry out one or more curative processing steps.

14. The surgical system of claim 13, wherein the one or more curative processing steps comprise:

rebooting the surgical system;

resetting the surgical system to an initialized state; and notifying a user via a graphical user interface (GUI) of the presence of the leak or the hardware error.

15. The surgical system of claim 1, the controller further configured to initiate the self-test in response to the surgical pack being inserted into a console of the surgical system.

* * * * *